United States Patent
Jung et al.

(10) Patent No.: US 11,897,495 B2
(45) Date of Patent: Feb. 13, 2024

(54) DRUNK DRIVING PREVENTION SYSTEM AND METHOD THEREFOR

(71) Applicant: HYUNDAI MOBIS CO., LTD., Seoul (KR)

(72) Inventors: Yu Jin Jung, Uiwang-si (KR); Yeon Su Kim, Gunpo-si (KR); June Seung Lee, Yongin-si (KR); Chang Won Lee, Seoul (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 0 days.

(21) Appl. No.: 17/875,536

(22) Filed: Jul. 28, 2022

(65) Prior Publication Data
US 2023/0041464 A1 Feb. 9, 2023

(30) Foreign Application Priority Data

Aug. 5, 2021 (KR) .................. 10-2021-0103018
Aug. 5, 2021 (KR) .................. 10-2021-0103022
Aug. 5, 2021 (KR) .................. 10-2021-0103025

(51) Int. Cl.
  *B60W 50/14* (2020.01)
  *H04W 4/029* (2018.01)
  (Continued)

(52) U.S. Cl.
  CPC ......... *B60W 50/14* (2013.01); *B60H 1/00007* (2013.01); *B60H 1/008* (2013.01);
  (Continued)

(58) Field of Classification Search
  None
  See application file for complete search history.

(56) References Cited

U.S. PATENT DOCUMENTS

2005/0125117 A1* 6/2005 Breed .................. G07C 5/0808
  701/31.5
2014/0365142 A1 12/2014 Baldwin
  (Continued)

FOREIGN PATENT DOCUMENTS

JP 2005096663 A 4/2005
JP 2009-226992 A 10/2009
  (Continued)

OTHER PUBLICATIONS

Extended European Search Report dated Jan. 2, 2023 in corresponding European patent application No. 22187429.0.
Extended European Search Report dated Apr. 17, 2023 in corresponding European patent application No. 22187429.0.

*Primary Examiner* — Thomas S McCormack
(74) *Attorney, Agent, or Firm* — Novo TechIP International PLLC

(57) ABSTRACT

According to the present disclosure, a drunk driving prevention system including: an alcohol detection unit configured to detect a driver's inebriation through the breath test device provided in a vehicle; a computation unit configured, when the driver is detected to be in a drunk state by the alcohol detection unit, to compute a driving-possible time at which the drunk state is resolved in the future so that driving is possible; and a notification unit configured to output the driving-possible time or whether or not driving is possible through an infotainment system of the vehicle or a driver's terminal is disclosed.

18 Claims, 15 Drawing Sheets

(51) Int. Cl.
  *B60H 1/00* (2006.01)
  *B60K 28/06* (2006.01)
  *B60N 2/00* (2006.01)
  *B60W 10/06* (2006.01)
  *B60W 40/08* (2012.01)
  *B60W 50/10* (2012.01)
  *G01N 33/497* (2006.01)

(52) U.S. Cl.
  CPC ....... *B60H 1/00785* (2013.01); *B60K 28/063* (2013.01); *B60N 2/002* (2013.01); *B60W 10/06* (2013.01); *B60W 40/08* (2013.01); *B60W 50/10* (2013.01); *G01N 33/4972* (2013.01); *H04W 4/029* (2018.02); *B60H 2001/00114* (2013.01); *B60W 2040/0827* (2013.01); *B60W 2040/0836* (2013.01); *B60W 2040/0881* (2013.01); *B60W 2050/143* (2013.01); *B60W 2050/146* (2013.01); *B60W 2420/42* (2013.01); *B60W 2540/221* (2020.02); *B60W 2540/229* (2020.02); *B60W 2540/24* (2013.01); *B60W 2556/10* (2020.02)

(56) References Cited

U.S. PATENT DOCUMENTS

| | | |
|---|---|---|
| 2015/0081134 A1 | 3/2015 | Burger |
| 2017/0096145 A1 | 4/2017 | Bahn |
| 2018/0289321 A1* | 10/2018 | Nothacker ............ A61B 5/4845 |
| 2019/0248237 A1* | 8/2019 | Albakri ................. B60W 50/14 |
| 2019/0299999 A1 | 10/2019 | Liu et al. |
| 2020/0202148 A1 | 6/2020 | Wright et al. |
| 2020/0398637 A1* | 12/2020 | Chang .................... G08B 21/22 |

FOREIGN PATENT DOCUMENTS

| | | |
|---|---|---|
| JP | 5348457 B2 | 11/2013 |
| KR | 1020040009435 A | 1/2004 |
| KR | 101705968 B1 | 10/2016 |
| WO | 20200101565 A1 | 5/2020 |
| WO | 2021/002796 A1 | 1/2021 |
| WO | 2021/041571 A1 | 3/2021 |

* cited by examiner (a) Only driver is on board (b) Both driver and passenger are on board

DRUNK DRIVING PREVENTION SYSTEM AND METHOD THEREFOR

CROSS-REFERENCE TO RELATED APPLICATIONS

This application claims the benefit of priority under 35 U.S.C. 119 to Korean Patent Application Nos. 10-2021-0103018, filed on Aug. 5, 2021, 10-2021-0103022, filed on Aug. 5, 2021, and 10-2021-0103025, filed on Aug. 5, 2021 in the Korean Intellectual Property Office, the disclosure of which is incorporated herein by reference in their entirety.

TECHNICAL FIELD

The present disclosure relates to a technology for informing of whether or not a driver is able to drive a vehicle at a driving-possible time after the driver drinks.

BACKGROUND

In recent years, automobiles have been established as necessities of life, so that the number of automobiles is rapidly increasing. In order to drive a vehicle safely, the driver must be conscious of safety above all else, and an example of an accident caused by lack of safety awareness is a drunk driving accident.

Particular attention should be paid to drunk driving because drunk driving puts the life of others at risk, as well as injuring a driver's body and damaging a driver's property, and as drunk driving becomes a serious social problem, the penalties therefor are being strengthened.

In order to prevent such drunk driving, the law came into effect by which strictly legal penalties are imposed on the driver and by which the person in the passenger seat is also punished in the case of an accident caused by drunk driving, but this law is insufficient to prevent drunk driving accidents.

In addition, although a breathalyzer tester for drivers has been recently released, the driver may ignore the measurement result of such a tester and drive, and in this case, the tester is limited to the role of a simple tester.

In addition, since the conventional vehicle is not equipped with a separate device that prevents operation of the vehicle when the driver drinks and drives, it is impossible to prevent driving under the influence of alcohol in advance, and although police officers crack down on drunk driving, this crackdown process is pointed out as an inefficient cultural aspect, as well as causing inconveniences.

Accordingly, although a disclosure in which a breath test device is provided inside a vehicle has been proposed in the prior art, a technology is required to inform whether or not the driver is in the state capable of driving while the driver rests inside or outside the vehicle after drinking.

The description of the background art above is intended only to help understanding of the background of the present disclosure, and should not be regarded as acknowledging that it corresponds to the prior art already known to those of ordinary skill in the art.

SUMMARY

The present disclosure has been proposed to solve the above problem, and an objective of the present disclosure is to measure the driver's blood alcohol concentration and inform of the driving-possible time and whether or not driving is possible at the driving-possible time through an infotainment system of a vehicle or a driver's terminal on the basis of the blood alcohol concentration and the driver's body information, thereby preventing the driver from drinking and driving.

A drunk driving prevention system according to the present disclosure may include: a breath test device configured to detect carbon dioxide and alcohol content contained in a driver's breath when the driver performs breath authentication; an alcohol detection unit configured to detect a driver's inebriation through the breath test device; a computation unit configured, if (or when) the driver is detected to be in a drunk state by the alcohol detection unit, to compute a driving-possible time at which the drunk state is resolved in the future so that driving is possible; and a notification unit configured to output the driving-possible time or whether or not driving is possible through an infotainment system of a vehicle or a driver's terminal.

The drunk driving prevention system may further include an input unit to which a signal notification intention of the driver is input, and if the signal notification intention is input to the input unit, the notification unit may provide the driving-possible time or whether or not driving is possible at the driving-possible time through the infotainment system of the vehicle or the driver's terminal.

The drunk driving prevention system may further include a passenger detection unit configured to detect whether or not the driver is on board through a camera sensor or a seat sensor provided in the vehicle, and if the passenger detection unit consistently detects that the driver is on board, the notification unit may provide the driving-possible time or whether or not driving is possible at the driving-possible time through the infotainment system of the vehicle.

The notification unit may set the driving-possible time on the basis of the location of the driver detected through a function of a GPS provided in the terminal to detect the location.

The notification unit may be configured to determine a driver's sleep state on the basis of whether or not the terminal is operating and provide whether or not driving is possible after a driver's wake-up time detected through the operation or non-operation of the terminal.

The drunk driving prevention system may further include a control module configured to determine the driver's inebriation from the alcohol concentration detected by the breath test device to determine whether or not breath authentication is complete and, if the breath authentication fails, restrict starting of the vehicle, and the control module may include an air quality judgment control unit configured to check indoor air quality on the basis of the amount of carbon dioxide detected by the breath test device and perform predetermined air quality control depending on the detected amount of carbon dioxide.

The air quality judgment control unit may set three reference values for a measured amount of carbon dioxide, and the air quality judgment control unit may be configured to output a notification message if the measured amount of carbon dioxide reaches a first reference value, output an alarm if the measured amount of carbon dioxide reaches a second reference value, and control the vehicle to switch to an outdoor air circulation mode if the measured amount of carbon dioxide reaches a third reference value.

The air quality judgment control unit may be configured to check the amount of carbon dioxide detected by the breath test device after the vehicle is stopped and, if the amount of carbon dioxide detected after the vehicle is stopped increases to a predetermined reference value or more, provide a notification of occupant neglect to the driver.

The drunk driving prevention system may further include: a check unit configured to check whether or not the breath test device, which is provided in the vehicle and has a fan inside thereof to suck the driver's breath, thereby measuring the drunk state, operates; a passenger detection unit configured to detect whether or not a passenger is on board; and a control module configured to control the air conditioner of the vehicle to discharge hot air above a predetermined temperature therefrom, thereby sterilizing the inside of the breath test device, if the check unit identifies that the breath test device has been operated and if the passenger detection unit detects that all passengers have alighted.

The drunk driving prevention system may further include a humidity sensor configured to detect the humidity inside the vehicle, and the control module may control the air conditioner to discharge hot air above a predetermined temperature by controlling a cooling device or heating device included in the air conditioner on the basis of the humidity detected by the humidity sensor.

A drunk driving prevention method according to the present disclosure may include the steps of: detecting a driver's inebriation through a breath test device provided in a vehicle; if the driver is detected to be in a drunk state in the step of detecting the drunk state, computing a driving-possible time at which the drunk state is resolved in the future so that driving is possible; and outputting the driving-possible time or whether or not driving is possible through an infotainment system of the vehicle or a driver's terminal.

The drunk driving prevention method may further include: a step of inputting a signal notification intention of the driver; and a step of providing the driving-possible time or whether or not driving is possible at the driving-possible time through the infotainment system of the vehicle or the driver's terminal if the signal notification intention is input in the step of inputting.

The step of detecting the drunk state may include a step of measuring the driver's blood alcohol concentration detected by the breath test device, and the driving-possible time of the driver may be computed on the basis of previously input driver's physical information and the driver's blood alcohol concentration detected by the alcohol detection unit in the step of computing.

The drunk driving prevention method may further include a step of detecting whether or not the driver is on board through a camera sensor or a seat sensor provided in the vehicle, and the step of outputting may include a step of providing the driving-possible time or whether or not driving is possible at the driving-possible time through the infotainment system of the vehicle if it is consistently detected that the driver is on board in the step of detecting whether or not the driver is on board.

The step of outputting may include a step of providing whether or not driving is possible through the driver's terminal at the driving-possible time if it is detected that the driver has alighted in the step of detecting whether or not the driver is on board.

The drunk driving prevention method may further include a step of detecting a location of the driver through the terminal after the step of computing, and the step of outputting may include a step of setting the driving-possible time on the basis of the location of the driver detected in the step of detecting the location.

The step of detecting the location may include a step of determining whether or not the detected location of the driver is a predetermined location, and the step of outputting may include a step of providing whether or not driving is possible after a predetermined driver's wake-up time if the location of the driver is the predetermined location.

The drunk driving prevention method may further include a step of determining a driver's sleep state on the basis of operation of the terminal after the step of computing, and the step of outputting may include a step of, if it is determined that the driver is asleep in the step of determining the driver's sleep state on the basis of the operation of the terminal, providing whether or not driving is possible after the driver's wake-up time detected through the operation or non-operation of the terminal.

The drunk driving prevention method may further include a step of determining a driver's sleep state by detecting illuminance of light through an illuminance sensor provided in the terminal after the step of computing, and the step of outputting may include a step of determining that the driver is asleep if the illuminance of light is low in the step of determining the driver's sleep state by detecting the illuminance of light and providing whether or not driving is possible after the driver's wake-up time determined in the step of determining the driver's sleep state by detecting the illuminance of light.

The drunk driving prevention method may further include a step of determining the driver's sleep state through a heart rate sensor provided in the terminal to measure a driver's heart rate after the step of computing, and the step of outputting may include a step of providing whether or not driving is possible after the driver's wake-up time on the basis of the driver's sleep state determined in the step of determining the driver's sleep state through the heart rate sensor.

A drunk driving prevention system according to the present disclosure may detect the drunk state of a driver, compute a driving-possible time on the basis of the blood alcohol concentration and the driver's personal information, and guide the driver to prevent the driver from drinking and driving.

The drunk driving prevention system may recognize a driver's location through a terminal or a sensor inside a vehicle and provide the driver with a notification that driving is possible through an infotainment system of the vehicle when the driver is located inside the vehicle and through a terminal when the driver is located outside the vehicle, thereby improving convenience.

In addition, the drunk driving prevention system may determine the driver's sleep state through the driver's terminal and set a driving-possible notification time to not disturb the driver in sleep, thereby improving convenience.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
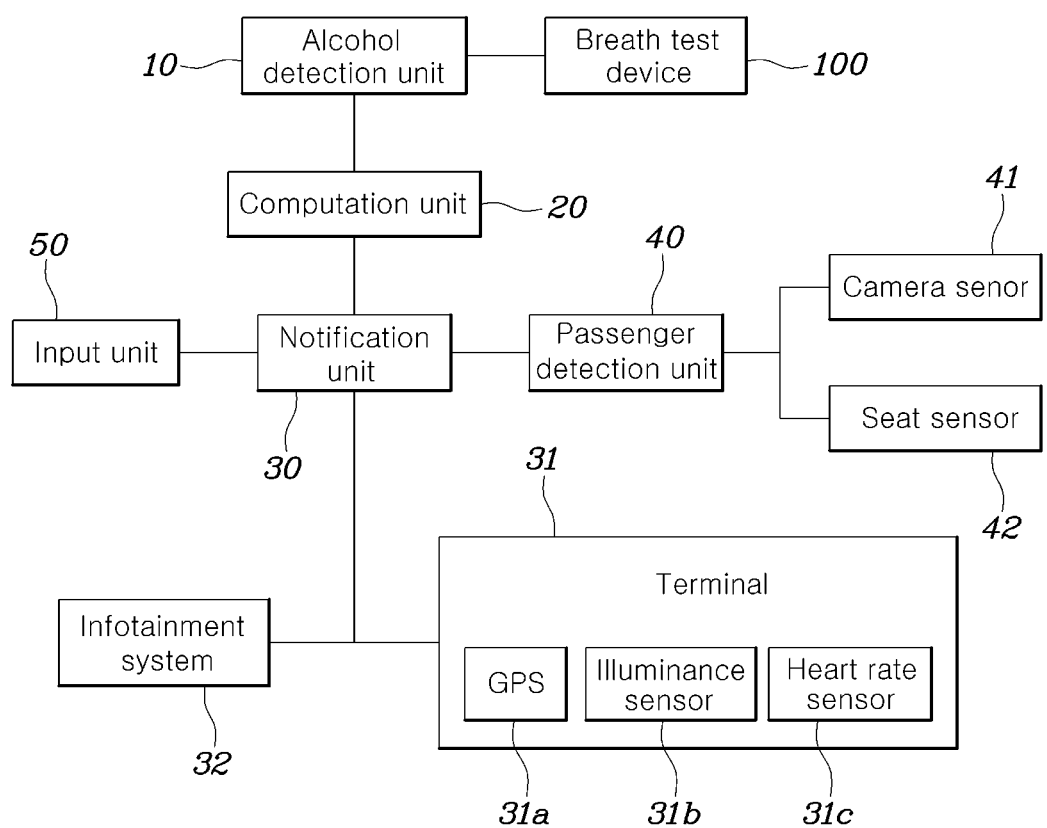
FIG. 1 is a block diagram of a drunk driving prevention system according to an embodiment of the present disclosure.

A specific structural or functional description of embodiments of the present disclosure set forth in the specification or application is given merely for the purpose of describing the embodiment according to the present disclosure. Therefore, the embodiments according to the present disclosure may be implemented in various forms, and the present disclosure should not be construed as being limited to the embodiments described in the specification or application.

Various changes and modifications may be made to the embodiments according to the present disclosure, and therefore particular embodiments will be illustrated in the drawings and described in the specification or application. However, it should be understood that embodiments according to the concept of the present disclosure are not limited to the particular disclosed embodiments, but the present disclosure includes all modifications, equivalents, and alternatives falling within the spirit and scope of the present disclosure.

Such terms as "a first" and/or "a second" may be used to describe various elements, but the elements should not be limited by these terms. These terms are intended merely to distinguish one element from other elements. For example, a first element may be named a second element and similarly a second element may be named a second element without departing from the scope of protection of the present disclosure.

In the case where an element is referred to as being "connected" or "accessed" to other elements, it should be understood that not only the element is directly connected or accessed to the other elements, but also another element may exist between them. Contrarily, in the case where a component is referred to as being "directly connected" or "directly accessed" to any other component, it should be understood that there is no component therebetween. The other expressions of describing a relation between structural elements, i.e., "between" and "merely between" or "neighboring" and "directly neighboring", should be interpreted similarly to the above description.

The terms used in the present disclosure are merely used to describe specific embodiments, and are not intended to limit the present disclosure. A singular expression may include a plural expression unless they are definitely different in a context. As used herein, the expression "include" or "have" are intended to specify the existence of mentioned features, numbers, steps, operations, elements, components, or combinations thereof, and should be construed as not precluding the possible existence or addition of one or more other features, numbers, steps, operations, elements, components, or combinations thereof.

Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure.

Hereinafter, exemplary embodiments of the present disclosure will be described in detail with reference to the accompanying drawings. Similar or like reference signs presented in the respective drawings designate similar or like elements.

A control unit (controller) according to exemplary embodiments of the present disclosure may be implemented by a non-volatile memory (not shown) which is configured to store data pertaining to an algorithm configured to control operations of various vehicle components or software instructions for reproducing the algorithm, and a processor (not shown) which is configured to perform the operations as described below by using the data stored in the corresponding memory. Here, the memory and the processor may be implemented as individual chips. Alternatively, the memory and the processor may be implemented as an integrated single chip. The processor may be in the form of one or more processors.

An alcohol detection unit 10, a computation unit 20, a notification unit 30, and a passenger detection unit 40 according to an exemplary embodiment of the present disclosure may be implemented through an algorithm configured to control the operation of various components of a vehicle or a non-volatile memory (not shown) configured to store data related to software instructions to execute the algorithm, and a processor (not shown) configured to perform operations described below using data stored in the memory. Here, the memory and the processor may be implemented as separate chips. Alternatively, the memory and processor may be implemented as a single integrated chip. The processor may be configured in the form of one or more processors.

FIG. 1 is a block diagram of a drunk driving prevention system according to an embodiment of the present disclosure.

A preferred embodiment of the drunk driving prevention system according to the present disclosure will be described with reference to FIG. 1.

A vehicle may be equipped with a breath test device 100 to check a drunk state of a driver before the operation of the vehicle in order to prevent the driver from driving under the influence of alcohol.

The breath test device 100 may be provided in the same form as an existing breath test device 100 and measure the driver's blood alcohol concentration through the driver's breathing, and the measured information may be transmitted to a vehicle's system.

A drunk driving prevention system according to the present disclosure may include an alcohol detection unit 10 for detecting a drunk state of the driver through the breath test device 100 provided in the vehicle; a computation unit 20 for computing, if the alcohol detection unit 10 detects that the driver is in the drunk state, a time at which the drunk state is resolved in the future so that driving is possible for the driver (hereinafter "driving-possible time"); and a notification unit 30 for outputting the driving-possible time or whether or not driving is possible through an infotainment system 32 of the vehicle or a driver's terminal 31.

The breath test device 100 provided adjacent to the driver's seat of the vehicle may measure the current blood alcohol concentration of the driver seated on the driver's seat, and the alcohol detection unit 10 may determine the driver's inebriation on the basis of the current blood alcohol concentration of the driver measured by the breath test device 100.

If the alcohol detection unit 10 detects that the driver is drunk because the driver's blood alcohol concentration is higher than a predetermined reference value, the computation unit 20 may compute a time at which the drunk state is resolved in the future so that the driver is able to drive the vehicle on the basis of the driver's blood alcohol concentration.

An input unit 50 to which a signal notification intention is input from the driver may be further included, and if the signal notification intention is input to the input unit 50, the notification unit 30 may provide the user with the driving-possible time or whether or not driving is possible at the driving-possible time through the infotainment system 32 of the vehicle or the driver's terminal 31.

The alcohol detection unit 10 may detect the driver's inebriation, and if it is detected that the driver is in the drunk state, the computation unit 20 may compute the time at which the driver's inebriation is resolved so that driving is possible, and the notification unit 30 may provide a message regarding whether or not to inform the driver of the driving-possible time through the infotainment system 32 of the vehicle, and the driver may input whether or not driving is possible through a touch screen or an input jog provided in the vehicle at the driving-possible time. The touch screen or input jog may be connected to the input unit 50 so that the intention input by the driver may be transmitted to the notification unit 30, and the notification unit 30 may or may not provide a notification that driving is possible (hereinafter "driving-possible notification") to the driver at the driving-possible time.

The alcohol detection unit 10 may detect the drunk state through the driver's blood alcohol concentration detected by the breath test device 100, and the computation unit 20 may compute the driving-possible time for the driver on the basis of previously input physical information of the driver and the driver's blood alcohol concentration detected by the alcohol detection unit 10.

When computing the time at which driving is possible, the computation unit 20 may compute the time at which the driver's inebriation is resolved on the basis of personal information such as the driver's age, gender, height, or weight input to the system and the blood alcohol concentration detected by the alcohol detection unit 10.

Through this, the time at which the driver's inebriation is resolved and at which driving is possible may be accurately calculated and then provided to the driver.

In addition, in the case of an unregistered driver, a new driver's personal information may be input through the infotainment system 32 of the vehicle, and the computation unit 20 may compute a driving-possible time for a new driver on the basis of the newly input personal information and a detected blood alcohol concentration.

A passenger detection unit 40 for detecting whether or not the driver is on board through a camera sensor 41 or a seat sensor 42 provided in the vehicle may be further included, and if the passenger detection unit 40 consistently detects the driver is on board, the notification unit 30 may inform of the driving-possible time or whether or not driving is possible at the driving-possible time through the infotainment system 32 of the vehicle.

The passenger detection unit 40 may be connected to the camera sensor 41 provided inside the vehicle to detect whether or not the driver is on board, and the input unit 50 may receive an input enabling notification that driving is possible at the driving-possible time after the drunk state of the driver is detected in the alcohol detection unit 10, and if the passenger detection unit 40 consistently detects that a passenger is on board for a predetermined time or longer, the notification unit 30 may provide the driver with a driving-possible notification at the driving-possible time through the infotainment system 32 or a speaker of the vehicle.

In addition, the passenger detection unit 40 may be connected to a sensor capable of detecting the driver, such as a $CO_2$ sensor of the vehicle or a pressure sensor mounted to the seat, as well as to the camera sensor 41, and detect whether or not the driver is on board.

Through this, a driving-possible notification may be provided to the driver who is resting inside the vehicle, guiding the driver to drive the vehicle safely at the driving-possible time, and it is possible to prepare for a drunk driving situation therethrough.

If the passenger detection unit 40 detects that the driver has alighted from the vehicle, the notification unit 30 may provide whether or not driving is possible through the driver's terminal 31 at the driving-possible time.

If the input unit 50 receives an input enabling notification that driving is possible at the driving-possible time after the drunk state of the driver is detected in the alcohol detection unit 10 and if the passenger detection unit 40 detects that the driver has alighted from the vehicle, the notification unit 30 may provide a notification that driving is possible through the driver's terminal 31 that is pre-registered and connected through wireless communication.

Through this, a driving-possible notification may be provided to the driver who is resting outside the vehicle at the driving-possible time, so that the driver may quickly get into the vehicle and drive safely, thereby preparing for a drunk driving situation.

The notification unit 30 may set the driving-possible time on the basis of the location of the driver detected through a function of a GPS 31A provided in the terminal 31 to detect the location.

The terminal 31 may include a driver's smartphone, and the driver's location may be identified through the GPS 31A function among the functions of the smartphone, and the driving-possible notification may be provided through the driver's terminal 31 when the driver is outside the vehicle and through the infotainment system 32 of the vehicle when the driver is inside the vehicle.

If a sensor for detecting a passenger is not provided inside the vehicle, the driver's location may be identified through the driver's terminal 31.

Through this, it may be applied to various types of vehicles.

If the driver's location detected through the terminal 31 corresponds to a predetermined location, the notification unit 30 may be configured to provide whether or not driving is possible after a predetermined driver's wake-up time.

If the driver's location recognized through the GPS 31A of the terminal 31 consistently corresponds to a predetermined location, the notification unit 30 may determine that the driver is sleeping and may provide the driving-possible notification through the driver's terminal 31 after a predetermined driver's wake-up time even if the driver sets the driving-possible notification at the driving-possible time through the input unit 50.

The predetermined location may be an accommodation or the driver's home, and other locations may be registered by the driver.

This has the effect of not disturbing the driver in sleep due to the driving-possible notification.

The notification unit 30 may be configured to determine the driver's sleep state on the basis of whether or not the terminal 31 is operating and to provide whether or not driving is possible after the driver's wake-up time detected through determining whether the terminal 31 is operational (awake) or nonoperational (sleep).

The notification unit 30 may be connected to the driver's terminal 31, determine the driver is asleep if a screen of the terminal 31 does not operate for a predetermined time or longer, determine that the driver has woken up through the operation or non-operation of the terminal 31, provide the driver with a driving-possible notification at the driving-possible time if the driver wakes up before the driving-possible time, and determine that the operation time of the terminal 31 is the driver's wake-up time if the driver is sleeping even at the driving-possible time so as to provide a driving-possible notification thereafter, not disturbing the driver in sleep.

The notification unit 30 may be configured, if the illuminance is detected to be low through an illuminance sensor 31b provided in the terminal 31, to determine that the driver is asleep and provide the driving-possible notification after the driver's wake-up time detected in the terminal 31.

The terminal 31 may be a smartphone, and the notification unit 30 may be connected to the driver's terminal 31, determine the ambient illuminance through the illuminance sensor 31b provided in the terminal 31, determine that the driver is asleep if the illuminance of the terminal 31 is low, determine that the driver has woken up through information of the illuminance sensor 31b indicating that the ambient illuminance of the terminal 31 is high, provide the driver with a driving-possible notification at the driving-possible time if the driver wakes up before the driving-possible time, and provide the driving-possible notification after the driver's wake-up time if the driver is still sleeping at the driving-possible time, not disturbing the driver in sleep.

The notification unit 30 may be configured to determine the driver's sleep state on the basis of a driver's heart rate detected through a heart rate sensor 31c provided in the terminal 31 and provide whether or not driving is possible after the driver's wake-up time detected by the terminal 31.

The terminal 31 may be a wearable device, and the notification unit 30 may be connected to the driver's terminal 31, detect a driver's heart rate through the heart rate sensor 31c provided in the terminal 31 to determine the driver's sleep state on the basis thereof, determine that the driver has woken up through the heart rate detected by the heart rate sensor 31c, provide the driver with a driving-possible notification at the driving-possible time if the driver wakes up before the driving-possible time, and provide the driving-possible notification after the driver wakes up if the driver is still sleeping at the driving-possible time, not disturbing the driver in sleep.

Figure 2:
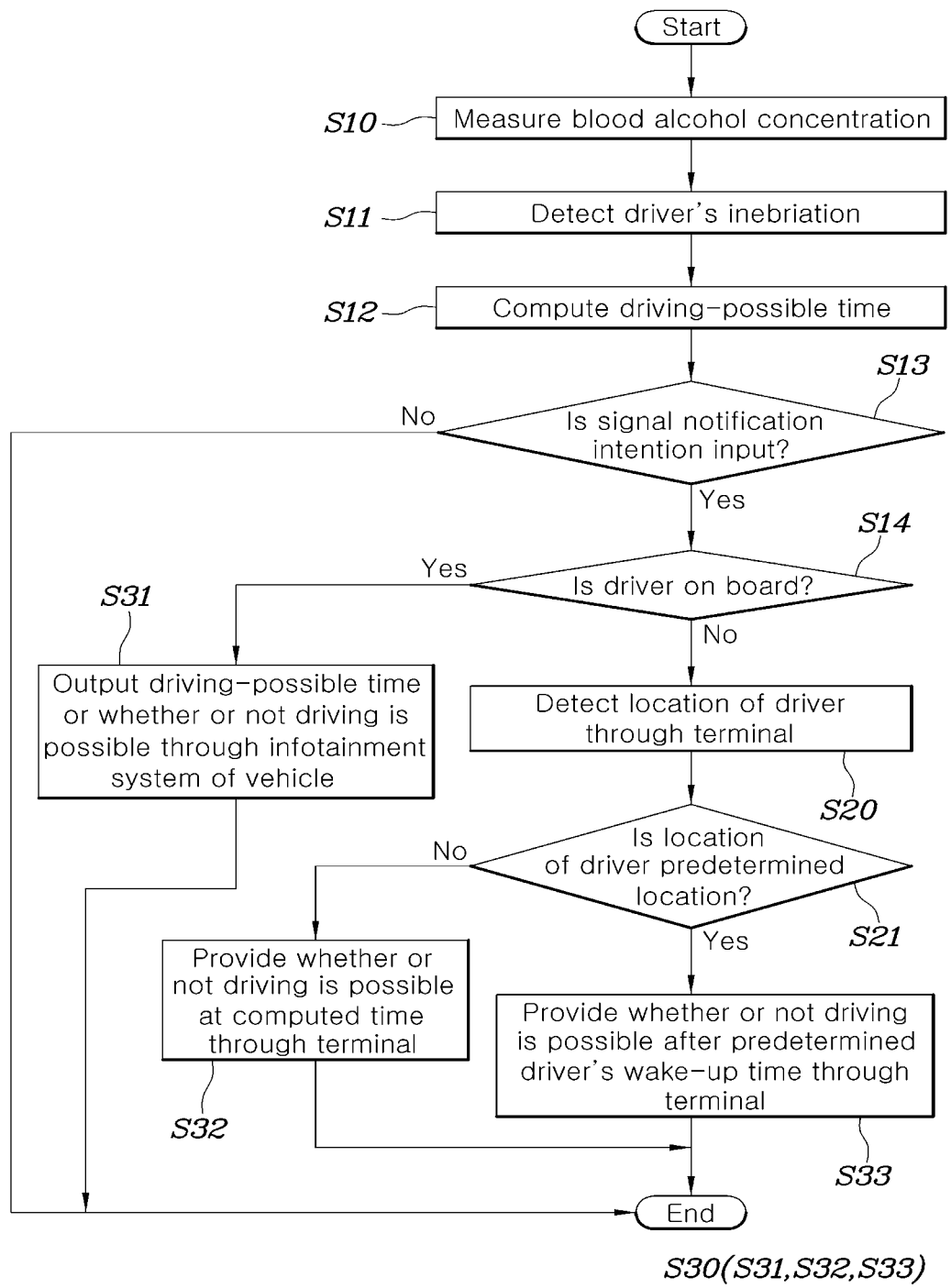
FIGS. 2 to 5 are flowcharts illustrating a method for preventing drunk driving according to an embodiment of the present disclosure.
Figure 3:
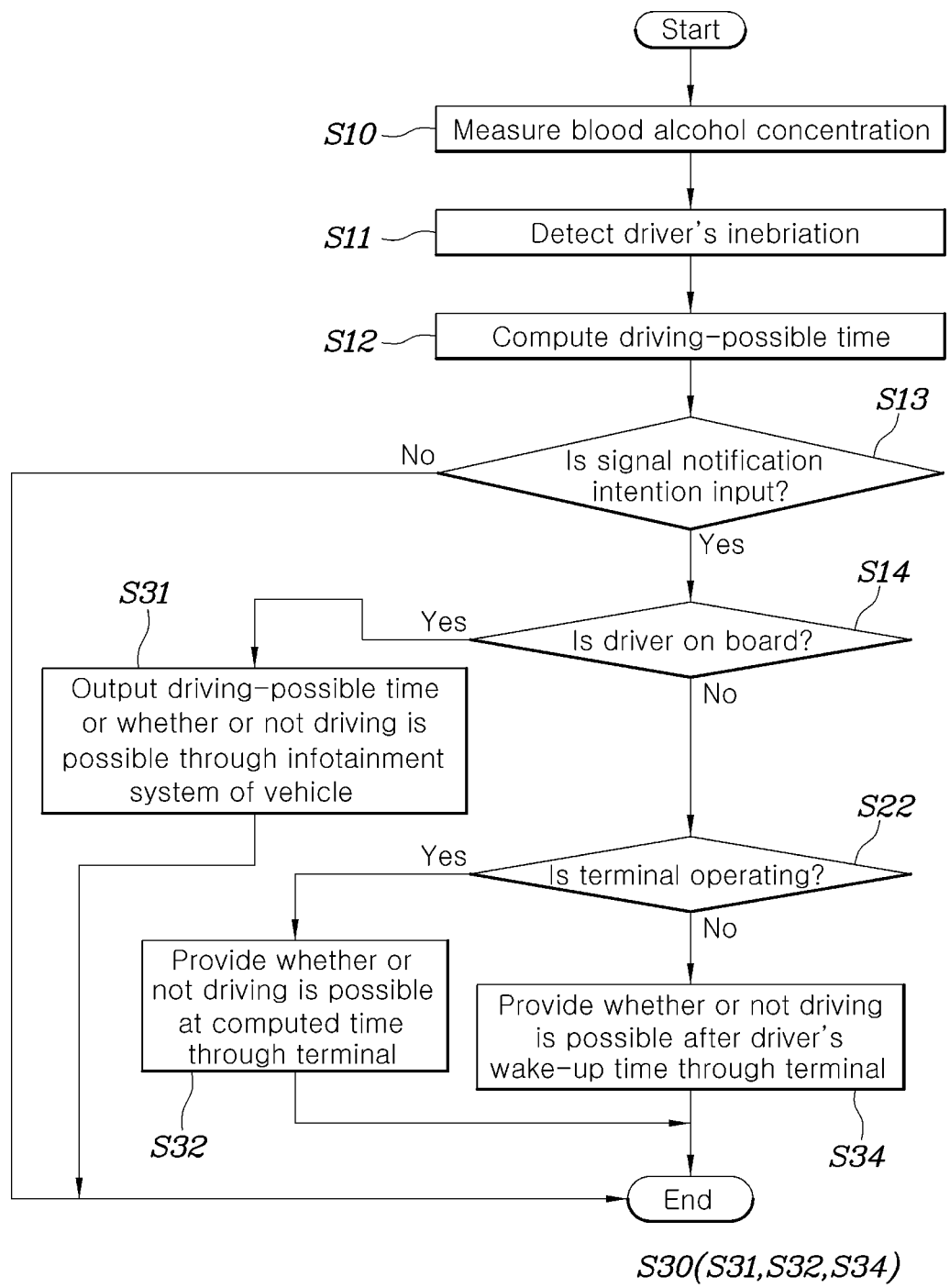
Figure 4:
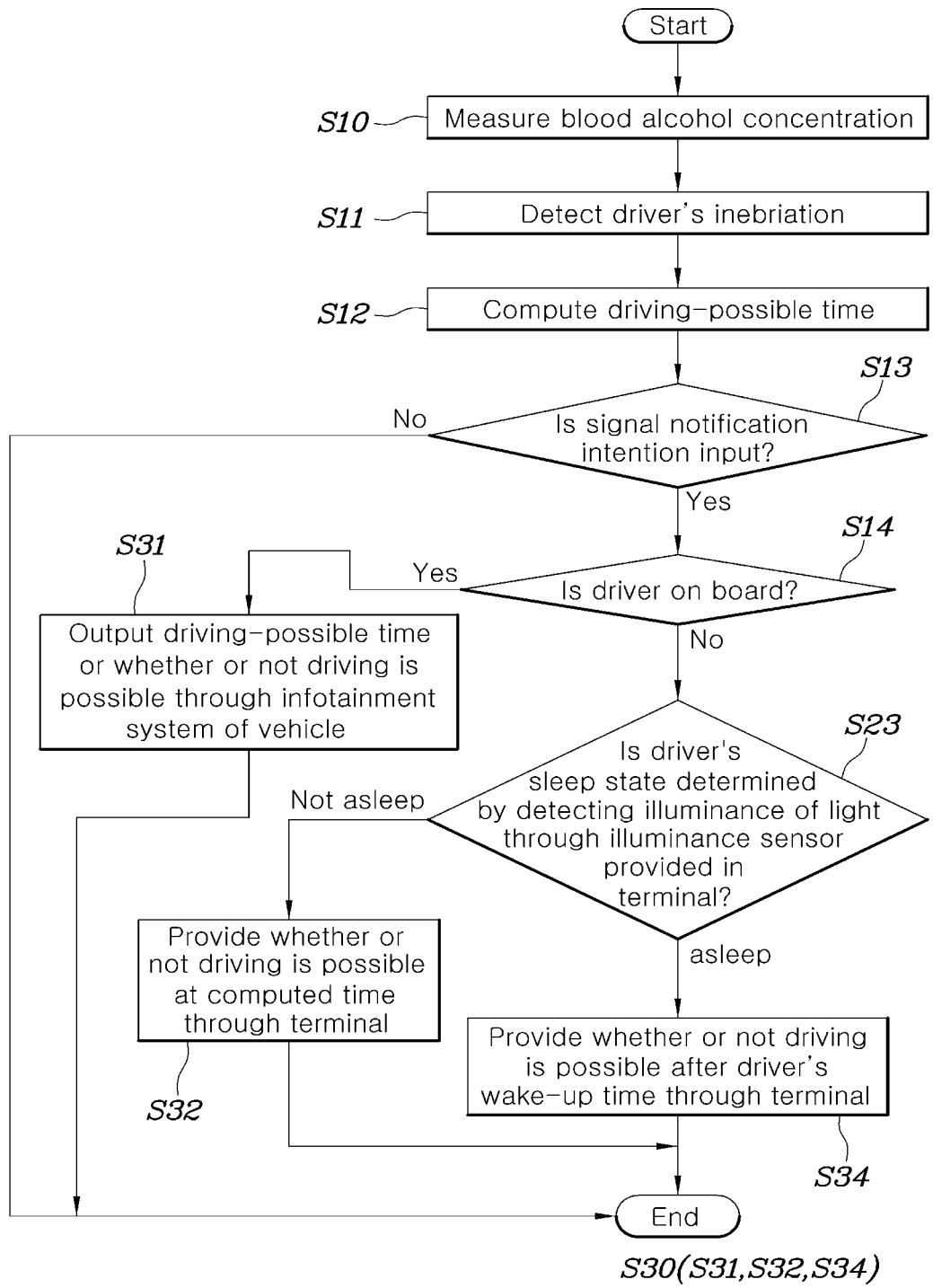
Figure 5:
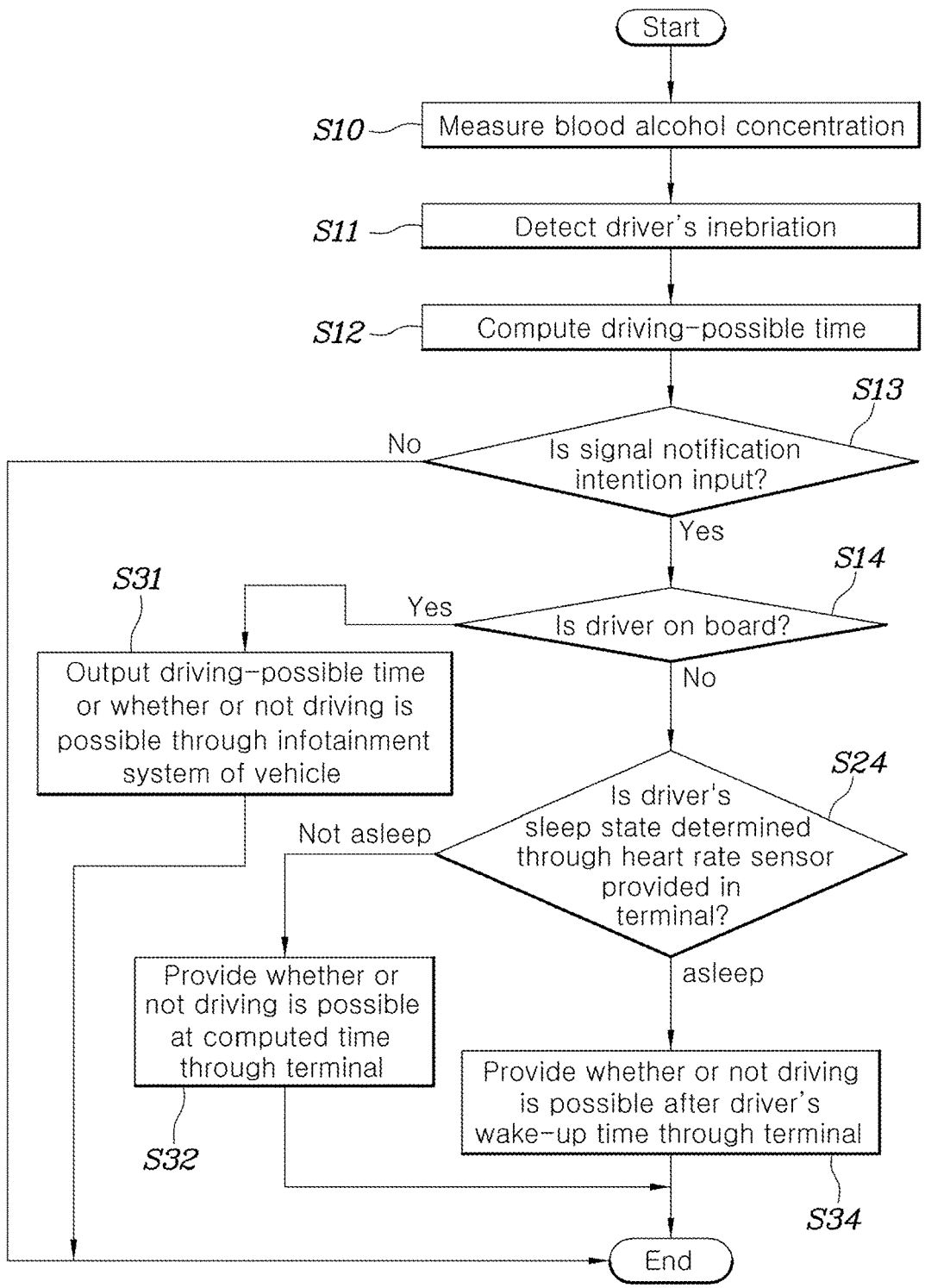

FIGS. 2 to 4 are flowcharts illustrating a method for preventing drunk driving according to an embodiment of the present disclosure.

A preferred embodiment of the drunk driving prevention method according to the present disclosure will be described with reference to FIGS. 2 to 4.

A drunk driving prevention method according to the present disclosure may include: a step S11 of detecting a driver's inebriation through a breath test device 100 provided in a vehicle; a step S12 of, if the driver is detected to be in a drunk state in the step S11 of detecting the drunk state, computing a driving-possible time at which the drunk state is resolved in the future so that driving is possible; and a step S30 of outputting the driving-possible time or whether or not driving is possible through an infotainment system 32 of the vehicle or a driver's terminal 31.

The drunk driving prevention method may further include a step S13 of inputting a signal notification intention of the driver, and if the signal notification intention is input in the step S13 of inputting, the driving-possible time or whether or not driving is possible may be provided at the driving-possible time through the infotainment system 32 of the vehicle or the driver's terminal 31 in the step S30 of providing.

The step S11 of detecting the drunk state may include a step S10 of measuring the driver's blood alcohol concentration detected by the breath test device 100, and the driving-possible time of the driver may be computed on the basis of previously input driver's physical information and the driver's blood alcohol concentration detected by the alcohol detection unit 10 in the step of computing.

The drunk driving prevention method may further include a step S14 of detecting whether or not the driver is on board through a camera sensor 41 or a seat sensor 42 provided in the vehicle, and the step S30 of outputting may include a step S31 of outputting the driving-possible time or whether or not driving is possible at the driving-possible time through the infotainment system 32 of the vehicle if it is consistently detected that the driver is on board in the step S14 of detecting whether or not the driver is on board.

The step S30 of outputting may include a step S32 of providing whether or not driving is possible through the driver's terminal 31 at the driving-possible time if it is detected that the driver has alighted in the step S14 of detecting whether or not the driver is on board.

The drunk driving prevention method may further include a step S20 of detecting a location of the driver through the terminal 31 after the step S12 of computing, and the step S30 of outputting may include a step of setting the driving-possible time on the basis of the location of the driver detected in the step S20 of detecting the location.

The step S20 of detecting the location may include a step S21 of determining whether or not the detected location of the driver is a predetermined location, and the step of outputting may include a step S33 of providing whether or not driving is possible after a predetermined driver's wake-up time if the location of the driver is the predetermined location.

The drunk driving prevention method may further include a step S22 of determining a driver's sleep state on the basis of operation of the terminal 31 after the step S12 of computing, and the step of outputting may include a step S34 of, if it is determined that the driver is asleep in the step S22 of determining the driver's sleep state on the basis of the operation of the terminal 31, providing whether or not driving is possible after the driver's wake-up time detected through the operation or non-operation of the terminal 31.

The drunk driving prevention method may further include a step S23 of determining a driver's sleep state by detecting illuminance of light through an illuminance sensor 31$b$ provided in the terminal 31 after the step S12 of computing, and the step of outputting may include a step S34 of determining that the driver is asleep if the illuminance of light is low in the step of determining the driver's sleep state by detecting the illuminance of light and providing whether or not driving is possible after the driver's wake-up time determined in the step of determining the driver's sleep state by detecting the illuminance of light.

The drunk driving prevention method may further include a step S24 of determining the driver's sleep state through a heart rate sensor 31$c$ provided in the terminal 31 to measure a driver's heart rate after the step S12 of computing, and the step of outputting may include a step S34 of providing whether or not driving is possible after the driver's wake-up time on the basis of the driver's sleep state determined in the step of determining the driver's sleep state through the heart rate sensor 31$c$.

Hereinafter, a drunk driving prevention system and a drunk driving prevention method using the same according to various embodiments of the present disclosure will be described in detail with reference to the accompanying drawings.

Figure 6:
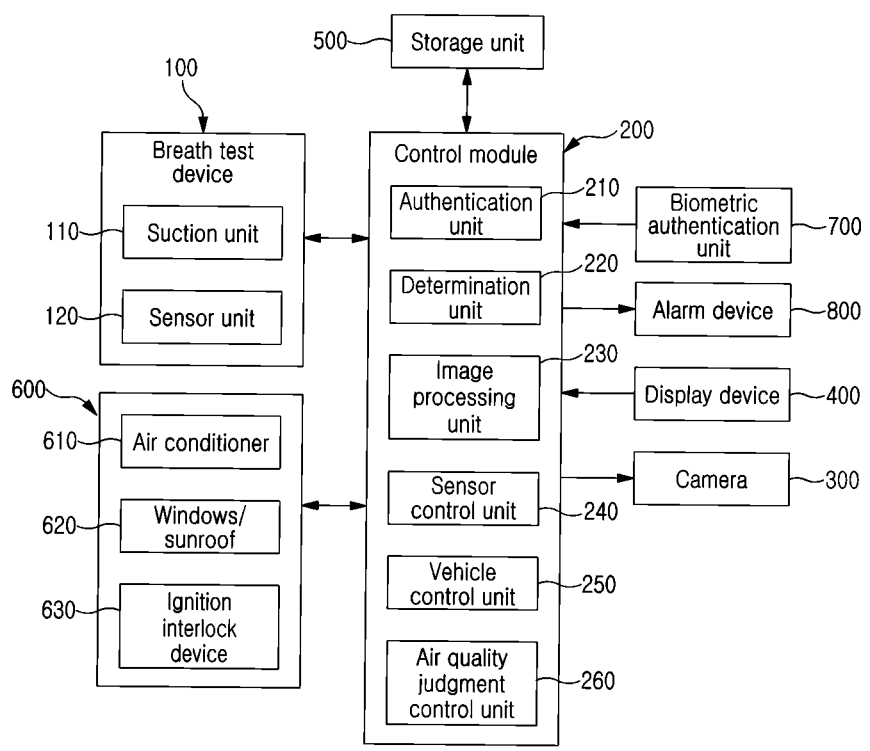
FIG. 6 is the configuration diagram of a drunk driving prevention system using indoor monitoring according to an embodiment of the present disclosure.

FIG. 6 is the configuration diagram of a drunk driving prevention system using indoor monitoring according to an embodiment of the present disclosure.

As shown in FIG. 6, the drunk driving prevention system according to a preferred embodiment of the present disclosure may include a camera 300 for photographing an image including a face of a driver seated on the driver's seat, a breath test device 100 for detecting alcohol contained in the driver's breath, and a control module 200 for identifying the driver on the basis of the image photographed by the camera 300 and detecting the driver's inebriation from the alcohol concentration detected by the breath test device 100, thereby operating an ignition interlock device 630 of the vehicle.

The camera 300 may be installed near the driver's seat inside the vehicle and may be configured to photograph the driver seated on the driver's seat. The camera 300 may be configured to transmit information about the photographed image to the control module 200 such that the control module 200 may process a subsequent procedure such as driver authentication based on the photographed driver image.

In addition, the drunk driving prevention system according to a preferred embodiment of the present disclosure may include a storage unit 500 capable of storing a variety of information such as information of the image photographed by the camera 300, information about alcohol detected by the breath test device 100, and the like, and a display device 400 capable of displaying a variety of information related to a breath authentication procedure to the driver. The display device may be a display device inside the vehicle, and preferably, may be a navigation device having a display unit such as an AVN (audio, video, and navigation) device or a cluster.

In particular, the drunk driving prevention system according to a preferred embodiment of the present disclosure may be a system that implements a bypass mode, including the control module 200 and the breath test device in a narrow sense, and may be a system including configurations such as a camera, a storage unit, and a display device in a broad sense. However, even the system in a narrow sense does not exclude the configurations of the camera and the storage unit, and the system may be implemented in a manner in which the camera, the storage unit, the display device provided in the vehicle system are interlocked with the control module 200 and the breath test device.

According to a preferred embodiment of the present disclosure, the breath test device 100 may take in the driver's breath to detect the amount of respiration and the alcohol concentration contained in the driver's breath. To this end, the breath test device 100 may include a suction unit 110 for sucking the driver's breath and a sensor unit 120 having an alcohol sensor for detecting alcohol contained in the driver's breath.

The suction unit 110 may be installed near the driver's seat at a location where the breath exhaled by the driver may be easily taken in, and preferably, may be installed near a cluster, a steering wheel, or a center fascia.

In particular, a fan driven by a motor may be installed in the suction unit 110 of the breath test device 100 so as to increase or reduce the amount of air intake by controlling the rotation speed of the fan. The fan may be installed in an inlet of the suction unit 110, and the operation of the motor for driving the fan may be controlled by a control unit of the breath test device 100 itself or a sensor control unit 240 in the control module 200.

In addition, the sensor unit 120 is configured to detect the amount of respiration through the suction unit 110 and detect an alcohol content contained in the intake air. In this regard, the sensor unit may include a carbon dioxide sensor for measuring the amount of respiration and an ethanol sensor to detect the alcohol concentration in the driver's breath. In addition, an optical sensor capable of detecting the alcohol content from the breath in an optical manner may be applied to the breath test device.

The carbon dioxide sensor is capable of measuring the amount of carbon dioxide contained in the person's breath, so the amount of respiration of the driver may be detected through the carbon dioxide sensor, and, based on this, it may be checked whether or not the amount of respiration of the driver is enough to be reliable in detecting the alcohol concentration.

Information on the detected amount of respiration and information on the alcohol content may be transmitted to the control module 200. Accordingly, the control module 200 may compare the information on the measured amount of respiration and the alcohol concentration information with a predetermined reference concentration to determine whether or not the driver is drunk or whether or not the driver is able to drive the vehicle.

The drunk driving prevention system according to a preferred embodiment of the present disclosure may include a display device for displaying a variety of information, and the display device 400 may be a display of a vehicle cluster, or other types of displays may be separately provided.

The display device 400 may be configured to output a variety of information that needs to be provided to the driver during the operation of the drunk driving prevention system and, in particular, may be configured to display a result of monitoring the indoor air quality and guidance information related to the required action or follow-up control according thereto.

For example, the display device 400 may be configured to provide a notification message such as a notification of information about the amount of indoor carbon dioxide or warning of falling asleep at the wheel, or provide vehicle state change information such as a change to an outdoor air circulation mode or opening a window according to the result of monitoring indoor air quality while the vehicle is driving after completion of breath authentication. In addition, the display device may provide image and sound information for an occupant left unattended in the vehicle under certain driving conditions.

The drunk driving prevention system according to the present disclosure may include a storage unit 500. The storage unit 500 may store a variety of information such as information about images photographed by the camera 300 in relation to a breath authentication procedure, information about alcohol detected by the breath test device 100, and the like. The image information may include information such as a photographing time, a driver's face, and the like.

In addition, the storage unit 500 may be configured to store camera information captured when an abnormality is detected inside the vehicle after the driver alights. The information stored in the storage unit may be transmitted to the server by a communication module inside the vehicle.

In addition, the storage unit 500 may store vehicle information including a window open/closed state and an air conditioner operation state before starting breath authentication. Since it is preferable to check the driver's inebriation in an indoor air circulation mode in which windows/sunroof 620 are all closed for accurate measurement, the control module 200 may perform control to close the windows/sunroof 620 of the vehicle and switch the vehicle to the indoor air circulation mode when the breath authentication is started. To this end, a vehicle control unit 250 of the control module 200 may be configured to output control commands for controlling the opening/closing of the windows/sunroof 620 of the vehicle or the indoor/outdoor air circulation mode of the air conditioner. In addition, the vehicle control unit 250 may perform control to close the vehicle doors in order to perform breath authentication.

At this time, information pre-stored before breath authentication may indicate information about the surrounding environment set by the driver before checking the drunk state, and thus, after completion of breath authentication, the control module 200 may perform control to switch the vehicle state according to the vehicle information before the breath authentication stored in the storage unit 500 so that the devices 600 inside the vehicle may return to the previous state set by the driver. However, since the vehicle doors cannot be controlled to be open, it is preferable that the state thereof is not stored in the storage unit 500.

The drunk driving prevention system according to a preferred embodiment of the present disclosure may further include a biometric authentication unit 700 for authenticating the driver. The biometric authentication unit 700 is intended to identify the current driver's information and may be configured as a biometric authentication device capable of authenticating the driver's fingerprint or iris information.

The storage unit 500 may pre-store biometric authentication information of a specific driver, and an authentication unit 210 may be configured to compare the stored biometric authentication information with the biometric authentication information of the current driver, which is authenticated through the biometric authentication unit 700, to perform a user authentication process.

In addition, the control module 200 may be configured to be connected to other components in the system, such as the breath test device 100, the camera 300, the display device 400, and the storage unit 500, by a communication interface and control the overall system according to the information transmitted from the components.

The control module 200 may be configured to include an authentication unit 210, a determination unit 220, an image processing unit 230, a sensor control unit 240, a vehicle control unit 250, and an air quality judgment control unit 260. The respective components included in the control module 200 are classified according to functions performed by the control module 200, and the respective components divided in the control module 200 are not necessarily separated physically. The remaining components, excluding the air quality judgment control unit 260 from the components of the control module 200, that is, the authentication unit 210, the determination unit 220, the image processing unit 230, the sensor control unit 240, and the vehicle control unit 250, are provided by way of example to explain general functions of the drunk driving prevention system, and any configurations capable of implementing the drunk driving prevention system even with the exclusion of some components thereof may be applied to the control module 200 of the present disclosure. In addition, the respective components in the control module 200 may be configured to be able to communicate with each other.

The control module 200 in a preferred embodiment of the present disclosure is a controller capable of performing various functions such as breath authentication, determination of a drunk state, and vehicle control, and may be configured to include a processor that performs computations so as to perform the above functions, a memory storing an algorithm for the processor to perform functions, and the like. In addition, the control module 200 may be provided by modularizing the authentication unit 210, the determination unit 220, the sensor control unit 240, the vehicle control unit 250, and the air quality judgment control unit 260. In addition, the subcomponents of the control module 200 described above are provided by way of example, and the control module 200 may be configured to perform the same or corresponding function while communicating with other vehicle controllers, and in this case, some subcomponents may be excluded or replaced.

With regard to the fundamental configuration of the control module 200, the authentication unit 210 is a configuration that performs the overall breath authentication procedure, and the determination unit 220 may compare the alcohol concentration detected in the breath test device 100 with a reference concentration, thereby detecting the driver's inebriation.

The authentication unit may check whether or not the driver is seated from information provided from a device such as a weight sensor of the driver's seat or a camera 300 photographing the driver's seat, and may identify the driver from an image photographed by the camera 300. In addition, the authentication unit 120 may be configured to determine whether or not breath authentication is completed on the basis of the amount of driver's respiration supplied to the breath test device 100.

Here, breath authentication indicates a procedure in which the driver's breath is sucked such that the breath test device 100 may detect the alcohol content included in the driver's breath and in which whether or not the driver is drunk is determined on the basis of the alcohol content detected by the breath test device. In addition, the completion of breath authentication indicates that the breath authentication is completed to be suitable for driving by the control module 200 because the alcohol concentration contained in the driver's breath is within a reference value.

For example, when the breath authentication is initiated by the authentication unit 210, the breath test device 100 may detect the alcohol content included in the driver's breath, and information about the detected alcohol content may be transmitted to the control module 200 so that the determination unit 220 of the control module 200 may compare the alcohol concentration detected in the breath test device 100 with a reference concentration to determine the drunk state of the driver.

As a result of the comparison, if it is determined that the driver is in the drunk state exceeding the reference concentration, the determination unit 220 may determine that driving is impossible due to the drunk state of the driver (failure of breath authentication) and operate the ignition interlock device 630 through the vehicle control unit 250 of the control module 200. In this regard, the ignition interlock device 630 indicates a device that restricts starting of a vehicle so that driving is impossible, and may be, for example, a device that cuts off the ignition power. On the other hand, if the detected driver's alcohol concentration is within the reference concentration, it may be determined that the breath authentication is completed because it is suitable for driving.

The image processing unit 230 is intended to receive information about an image photographed by the camera 300 and process the same into image information necessary for the control module 200. The sensor control unit 240 is intended to control the breath test device, and may control the rotation speed of a fan of the breath test device 100, the sensitivity of the breath test device 100, and the like. The vehicle control unit 250 may be configured to transmit control commands to other vehicle interior devices 600 inside the vehicle, for example, vehicle doors, windows/sunroof 620, an air conditioner 610, and an ignition interlock device 630.

The air quality judgment control unit 260 may be configured to determine the indoor air condition on the basis of the amount of carbon dioxide detected by the breath test device and display the determined air quality condition to the outside through a display device. In addition, the air quality judgment control unit 260 may be configured to implement a predetermined air quality control on the basis of the current air quality condition.

Therefore, in the present specification, indoor air quality is a parameter determined according to an increase or decrease in the amount of indoor carbon dioxide. In general, when the amount of carbon dioxide increases in an enclosed space such as a vehicle interior, difficulty concentrating, headaches, and drowsiness may be induced, and, the American Industrial Hygiene Association has announced that when the concentration of carbon dioxide exceeds 2,000 ppm in an enclosed space, headaches or drowsiness are induced. In this regard, in the present specification, if the carbon dioxide exceeds a reference value, for example, 2,000 ppm, the air quality may be regarded as bad. However, this reference value is only an example, and the present disclosure is intended to define only tendency in which it is determined that indoor air quality deteriorates when the detected amount of carbon dioxide increases and that indoor air quality improves when the detected amount of carbon dioxide decreases on the basis of a predetermined value. In addition, a plurality of reference values may be used as the aforementioned reference value according to a detailed control method.

In addition, in the present disclosure, air quality control may be interpreted as a concept encompassing an alarm sound, a notification message, and direct vehicle control provided in the vehicle on the basis of the current amount of indoor carbon dioxide. For example, such air quality control includes a concept of outputting related notification messages (a notification of indoor air quality degradation, a request for ventilation, recommendation of rest, etc.) through a display device in order for the driver or a passenger to manually control devices inside the vehicle such as the air conditioner, the windows, and the like, as well as directly controlling the devices inside the vehicle to directly adjust the amount of carbon dioxide.

Meanwhile, in determining the amount of indoor carbon dioxide, the amount of carbon dioxide temporarily detected by the driver's breath is not a factor reflecting the indoor air quality and thus must be removed as noise when determining the same. As described above, since the breath test device is installed near the driver's seat to easily detect the driver's breath, the measured amount of carbon dioxide of the breath test device is sensitive to the driver's breath.

Therefore, the air quality judgment control unit 260 may be configured to check an increase in the amount of carbon dioxide temporarily detected by the driver's breath and in this case, even if the amount of carbon dioxide detected by the breath test device exceeds the reference value, to not perform air quality control is performed by way of exception. In a normal driving situation, in the drunk driving prevention system according to the present disclosure, the fan is controlled to consistently rotate in order to suck the indoor air through an intake of the breath test device. At this time, when the driver talks or sings, the amount of carbon dioxide detected by the breath test device greatly fluctuates temporarily.

Figure 9:
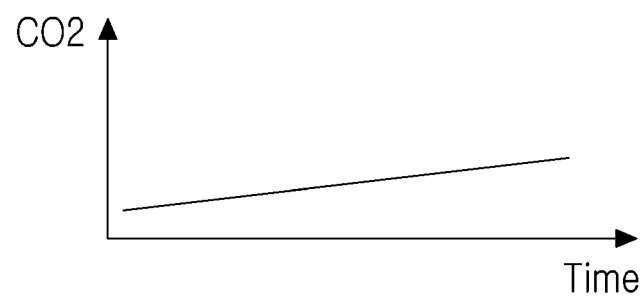
FIG. 9 is a graph showing an increase in the amount of carbon dioxide when driving in an indoor air circulation mode.
Figure 9:
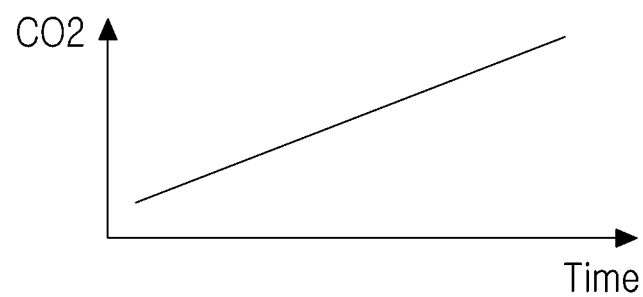

In this regard, FIG. 9 shows graphs illustrating an increase in the measured amount of carbon dioxide depending on the driver's breath in an indoor air circulation mode.

Figure 8:
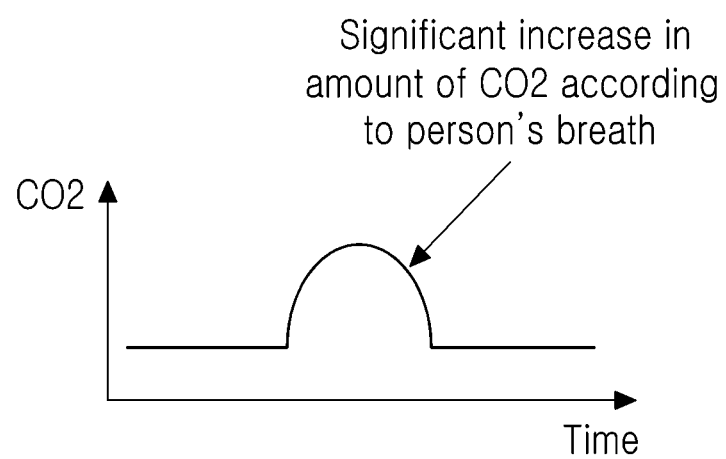
FIG. 8 is a graph showing a rapid increase in a measured amount of carbon dioxide according to the driver's breathing.

As shown in FIG. 9, in the case where the measured amount of carbon dioxide temporarily increases depending on the driver's breath, the air quality judgment control unit 260 may treat this as an exception and exclude the detection result from air quality control. At this time, in the case where the measured amount of carbon dioxide temporarily increases and then decreases again, the air quality judgment control unit 260 may determine that it results from the driver's breath. In general, since indoor air quality shows a certain level of increase as shown in FIG. 8 according to the driver's breath, when a change in the amount of carbon dioxide deviates greatly from this increase as shown in FIG. 8, it may be determined to be caused by the driver's breath. That is, the air quality judgment control unit 260 may be configured to identify a slope of the amount of change in the detected amount of carbon dioxide and set an acceptable range in which the determined slope changes. For example, the air quality judgment control unit 260 may be configured to detect in real time a slope value representing an increase in the currently detected carbon dioxide and may perform configuration such that if this value is within an acceptable reference range, for example, if the current slope value significantly changes by 10% or more, such a change in the slope is regarded as an exceptional circumstance so that air quality control is not applied.

Therefore, if the slope of a change in the currently identified amount of carbon dioxide deviates beyond a predetermined range and then recovers, it may be determined as a temporary change due to the driver's breath and may be treated as an input exception for air quality control.

In addition, in another embodiment of the present disclosure, the breath test device may be configured to directly determine whether or not the amount of carbon dioxide is temporarily increased by the driver's breath. In this case, the breath test device may process the amount of carbon dioxide temporarily increased by the breath as noise so as not to transmit the same to the air quality judgment control unit 260.

In addition, whether or not the amount of carbon dioxide temporarily increases due to the driver's breath may be determined on the basis of a change in the shape of the driver's mouth in the image photographed by the camera. However, it is preferable that the determination by the camera image is supplementarily made, and therefore, it is more preferable to determine whether or not it is due to the driver's breath by combining the information on the detection amount from the breath test device and the result of determining a change in the shape of the driver's mouth.

Meanwhile, the amount of indoor carbon dioxide increases by the occupant's breathing, whereas it decreases according to the degree to which outdoor air is introduced. Accordingly, the amount of carbon dioxide tends to increase when the occupants breathe in the state in which inflow of outdoor air is blocked, that is, in the indoor air circulation mode, and headaches or drowsiness may be induced due to the increased amount of carbon dioxide.

In this regard, FIG. 9 is a graph showing an increase in the amount of carbon dioxide when driving in an indoor air circulation mode. Graph (a) in FIG. 9 represents the case in which the driver rides alone, and graph (b) in FIG. 9 represents the case in which the driver and a passenger ride together, which show that the amount of indoor carbon dioxide tends to increase to a certain level at different slopes depending on the number of occupants. In the case where slope information about an increase in the amount of carbon dioxide depending on the number of occupants and the seating positions is pre-stored in the vehicle, position information of the occupants may be identified on the basis of the amount of carbon dioxide measured inside the vehicle, and for example, this information may be utilized to check whether or not an occupant is riding in a rear seat not having a seat sensor on the basis thereof.

On the other hand, when the vehicle is driving in the outdoor air circulation mode, since outdoor air is consistently introduced, the amount of carbon dioxide does not show a tendency to increase as shown in FIG. 9, so that deterioration of indoor air quality due to an increase in the amount of carbon dioxide may be unproblematic.

Therefore, according to a preferred embodiment of the present disclosure, the air quality judgment control unit 260 is preferably configured to perform the air quality control only when the vehicle is driving in the indoor air circulation mode. Therefore, the breath test device and the like may be turned off in the outdoor air circulation mode, thereby reduce power consumption.

However, since the air quality deterioration problem may occur even in the outdoor air circulation mode due to a filter condition, a failure of the air conditioner, etc., another example of the present disclosure may be configured such that the indoor air quality control is conducted even in the outdoor air circulation mode. In addition, the air quality control may be performed in the outdoor air circulation mode by the driver's selection.

An example of controlling the air quality by the air quality judgment control unit 260 will be described with reference to FIG. 10. In this regard, FIG. 10 is a graph showing an example of controlling a vehicle depending on a measured amount of carbon dioxide in a method of controlling indoor air quality of the vehicle using a drunk driving prevention system according to an embodiment of the present disclosure.

In indoor air quality control, it may be configured to set only one reference value and to perform predetermined control if a measured value reaches the set reference value.

Figure 10:
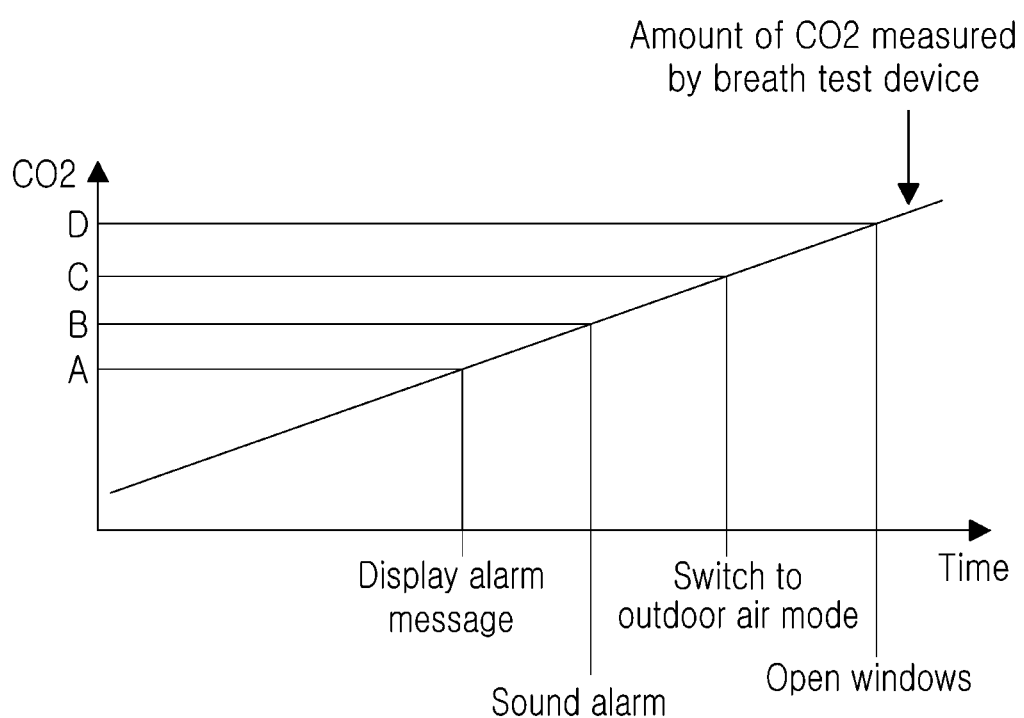
FIG. 10 is graphs showing an example of controlling a vehicle depending on a measured amount of carbon dioxide in a method of controlling indoor air quality of the vehicle using a drunk driving prevention system according to an embodiment of the present disclosure.

For example, the present disclosure may be configured such that only a value A in FIG. 10 is set as a reference value and such that the air quality judgment control unit 260 performs predetermined air quality control if the amount of carbon dioxide detected in the breath test device exceeds the reference value A. In this case, the air quality control may be to display a notification message notifying of deterioration of indoor air quality as shown in FIG. 10. In addition, such air quality control may be outputting an alarm so as to provide an immediate warning effect to the driver. As another example, the air quality control may be controlling the vehicle to switch to the outdoor air circulation mode by controlling the air conditioner of the vehicle. Alternatively, the system may be implemented such that windows are controlled to be temporarily opened. However, a specific method of controlling the air quality is not limited to the above examples, and any method capable of informing the occupants inside the vehicle of the indoor air quality information or controlling devices inside the vehicle to reduce the amount of indoor carbon dioxide may be applied without limitation.

Meanwhile, according to a preferred embodiment of the present disclosure, a plurality of reference values for the measured amount of carbon dioxide may be set in stages as shown in FIG. 10, and different air quality control methods may be pre-configured so as to be matched to the plurality of reference values. In this case, it is preferable that a direct and effective air quality control method is applied to a higher reference value and that a method of providing a notification to the driver without changing the driving condition is limited to a lower reference value. In this specification, regarding such a control method, the former will be referred to as "air quality improvement control" and the latter will be referred to as "notification control".

Regarding a specific control method, as shown in FIG. 10, the air quality judgment control unit 260 may be configured to store control methods for four reference values A, B, C, and D and sequentially perform control of displaying a notification message, sounding an alarm, switching to the outdoor air circulation mode, and opening windows when the respective reference values are reached. In this case, displaying a notification message and sounding an alarm are examples of the notification control described above, and switching to the outdoor air circulation mode and opening windows are examples of the air quality improvement control.

In addition, in another example of the present disclosure, it may be configured to perform control only for the reference values A, B, and C, that is, displaying a notification message, sounding an alarm, and switching to the outdoor air circulation mode, and opening windows, excluding the reference value D and control thereof. However, in such staged control, the number of the configured reference values and control related thereto are not limited to the illustrated examples, and any configuration capable of providing a notification to the inside of the vehicle or appropriately controlling the devices inside the vehicle may be applied, regardless of the number thereof and control methods.

The air quality judgment control unit 260 may be used for the purpose of determining the presence or absence of an occupant by checking indoor air quality when driving of the vehicle ends and when the driver alights from the vehicle.

Figure 11:
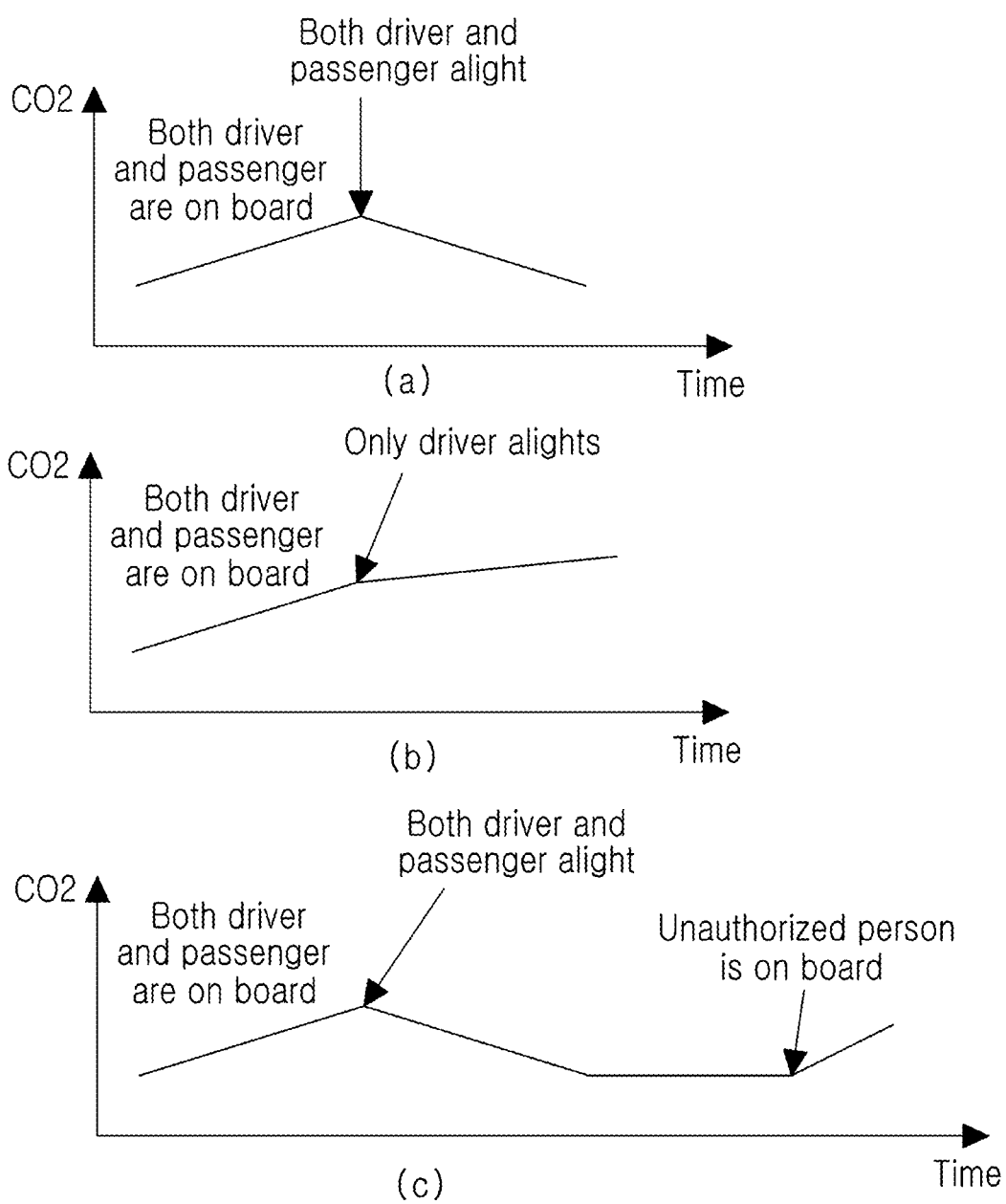
FIG. 11 is graphs showing a change in carbon dioxide inside a vehicle depending on passengers of the vehicle after a driver alights from the vehicle.

In relation to this, FIG. 11 shows a change in the amount of indoor carbon dioxide according to specific conditions after the operation of the vehicle is completed, the vehicle stops, and then a driver alights from the vehicle.

In particular, graph (a) in FIG. 11 indicates the case where both a driver and occupants alight from the vehicle and shows that a measured amount of carbon dioxide is gradually reduced when both the driver and the occupants alight.

On the other hand, if only the driver alights from the vehicle and if the occupants are still on board, as shown in graph (b) of FIG. 11, the measured amount of carbon dioxide keeps increasing, but only its slope decreases slightly. Accordingly, in the case where the measured amount of carbon dioxide continues to increase while the degree of increase in the measured amount of carbon dioxide changes as described above, the air quality judgment control unit 260 may determine that there is an occupant in the vehicle.

Meanwhile, in graph (a) of FIG. 11, when the vehicle is stopped and when then both the driver and the occupants alight from the vehicle, the amount of carbon dioxide is reduced at a constant slope, so that the amount of carbon dioxide remains at a certain level thereafter. In this state, the air quality judgment control unit 260 may activate an anti-theft function for monitoring an intrusion into the vehicle.

That is, as shown in graph (c) of FIG. 11, when an unauthorized person enters the vehicle by unlocking the door in an abnormal way without possessing the vehicle key, the amount of carbon dioxide inside the vehicle increases again. In this case, if such a change of state is detected by the breath test device, the air quality judgment control unit 260 may determine that there is an intrusion by an unauthorized person and perform control to inform the driver of the same.

In this regard, a notification of intrusion may be configured when a change in the amount of carbon dioxide exceeds a reference value within a certain period of time, and a vehicle theft detection notification may be provided to a smartphone registered by the driver or may be a warning sound output to the outside through a vehicle alarm device 800. Therefore, the air quality judgment control unit 260 may be configured, if the intrusion state by an unauthorized person is determined, to send a vehicle theft detection notification to the driver using a communication module inside the vehicle or output a warning sound to the outside of the vehicle through the alarm device 800.

Detailed steps of a method for monitoring and controlling the indoor state of a vehicle using the drunk driving prevention system having the above configuration will be described with reference to FIGS. 7 and 12.

Figure 12:
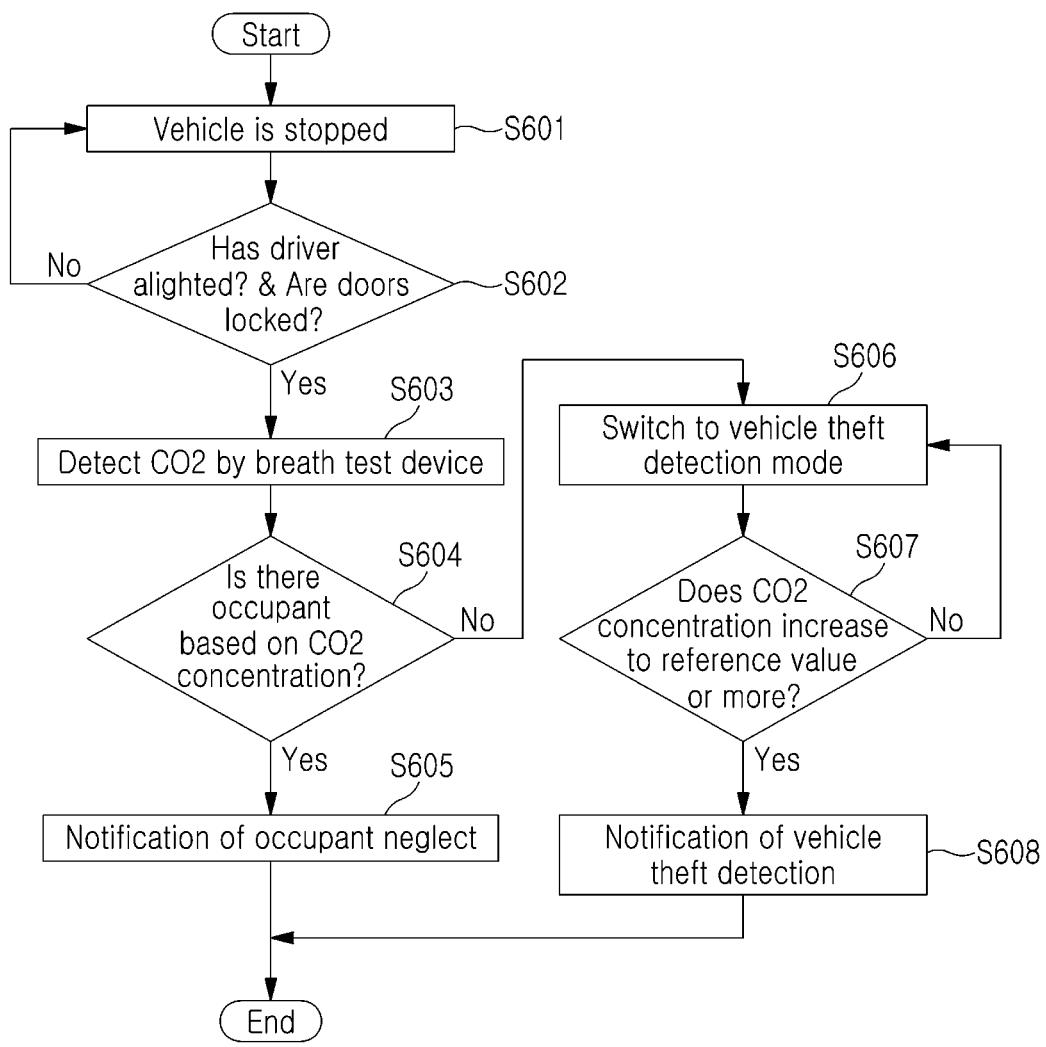
FIG. 12 is a flowchart illustrating an example of monitoring a vehicle state after a driver alights from the vehicle in a method of monitoring an indoor state of a vehicle using a drunk driving prevention system according to an embodiment of the present disclosure.

FIG. 2 is a flowchart illustrating a method for monitoring the indoor state of a vehicle and controlling air quality using a drunk driving prevention system according to an embodiment of the present disclosure, and FIG. 12 is a flowchart illustrating an example of monitoring a vehicle state after a driver alights and performing control according thereto.

A method for monitoring and controlling the indoor state of a vehicle using a drunk driving prevention system according to the present disclosure may include a step of detecting the amount of indoor carbon dioxide by a breath test device while the vehicle is driving and an air quality control step of checking the indoor air quality on the basis of the amount of carbon dioxide detected by the breath test device and performing a predetermined air quality control according to the detected amount of carbon dioxide.

Figure 7:
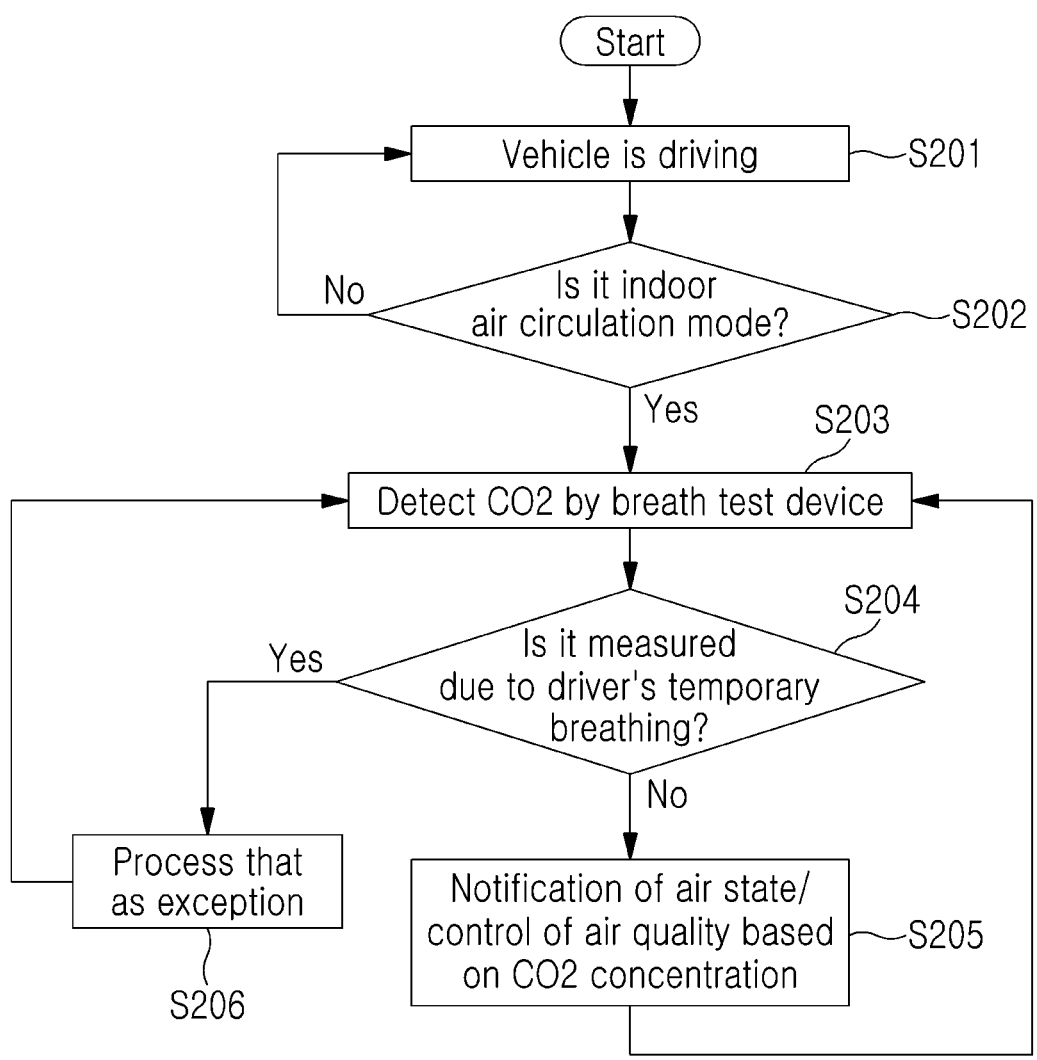
FIG. 7 is a flowchart illustrating a method of monitoring an indoor state of a vehicle and controlling air quality using a drunk driving prevention system according to an embodiment of the present disclosure.

Specifically, as shown in FIG. 7, while a vehicle is driving (S201), indoor air quality monitoring and control is performed on the basis of the amount of carbon dioxide detected by the breath test device.

In this regard, the control module 200 may be configured to check whether or not the vehicle is driving in an indoor air circulation mode (S202) and to perform air quality control only when the vehicle is driving in the indoor air circulation mode. On the other hand, in an outdoor air circulation mode, air quality control is not performed until the vehicle switches to the indoor air circulation mode.

If the vehicle is driving in the indoor air circulation mode, a step S203 of detecting carbon dioxide inside the vehicle is performed by the breath test device.

The breath test device may be configured, in detecting carbon dioxide in real time and performing air quality control, to check whether or not a value is measured due to driver's temporary breathing (S204) and, if it is measured due to driver's temporary breathing, process the same as an exception so as not to perform related air quality control even if a measured amount of carbon dioxide exceeds a specific reference value (S206).

Meanwhile, if it is determined that the detected amount of carbon dioxide is not caused by the driver's breathing, the air quality judgment control unit performs predetermined air quality control on the basis of the detected amount of carbon dioxide (S205).

A detailed method of air quality control is the same as described above.

Such control may continue until the operation of the vehicle is terminated so that the vehicle is stopped, and in some cases, the related control may be terminated when the vehicle switches to the outdoor air circulation mode or when a window is opened.

Meanwhile, a method for monitoring and controlling the indoor state of the vehicle depending on the presence or absence of an occupant after the vehicle is stopped will be described with reference to FIG. 12.

As shown in FIG. 12, when vehicle driving is finished and then the vehicle is stopped (S601), the driver alights from the vehicle and checks whether or not doors are locked (S602). In this regard, it is possible to check whether or not the driver alights from the vehicle through information from a camera, a seat sensor, or the like, and it is possible to check whether or not the doors are locked through a vehicle door sensor.

When the driver alights from the vehicle and when the doors are locked, it may be assumed that the driver is moving with the intention of leaving the vehicle. In this case, if there is an occupant inside the vehicle, it is highly likely that the driver and the like have accidentally left the occupant in the vehicle and moved.

Accordingly, in a preferred embodiment of the present disclosure, it is configured to detect carbon dioxide by the breath test device (S603) in the above case, that is, in the case where the driver alights from the vehicle and where the doors are locked, check whether or not there is an occupant according to the detected result (S604), and provide a notification of occupant neglect (S605). For example, if the amount of carbon dioxide detected after the vehicle is stopped increases to a predetermined reference value or more, it may be determined that there is an occupant, and a notification of occupant neglect may be provided to the driver.

Meanwhile, if the amount of carbon dioxide detected after the vehicle is stopped falls to a predetermined reference value or less as shown in (c) of FIG. 11, the vehicle may switch to a vehicle theft detection mode (S606). In the vehicle theft detection mode, the amount of carbon dioxide detected by the breath test device may be identified (S607), and if the detected amount of carbon dioxide increases to a predetermined reference value or more, it may be determined that an unauthorized person has intruded, thereby providing a vehicle theft detection notification (S608).

As described above, the drunk driving prevention system and method may be utilized for various purposes such as indoor air quality control, notification of occupant neglect, vehicle theft detection, and the like, as well as blood alcohol measurement, thereby improving the usability of the drunk driving prevention system.

Figure 13:
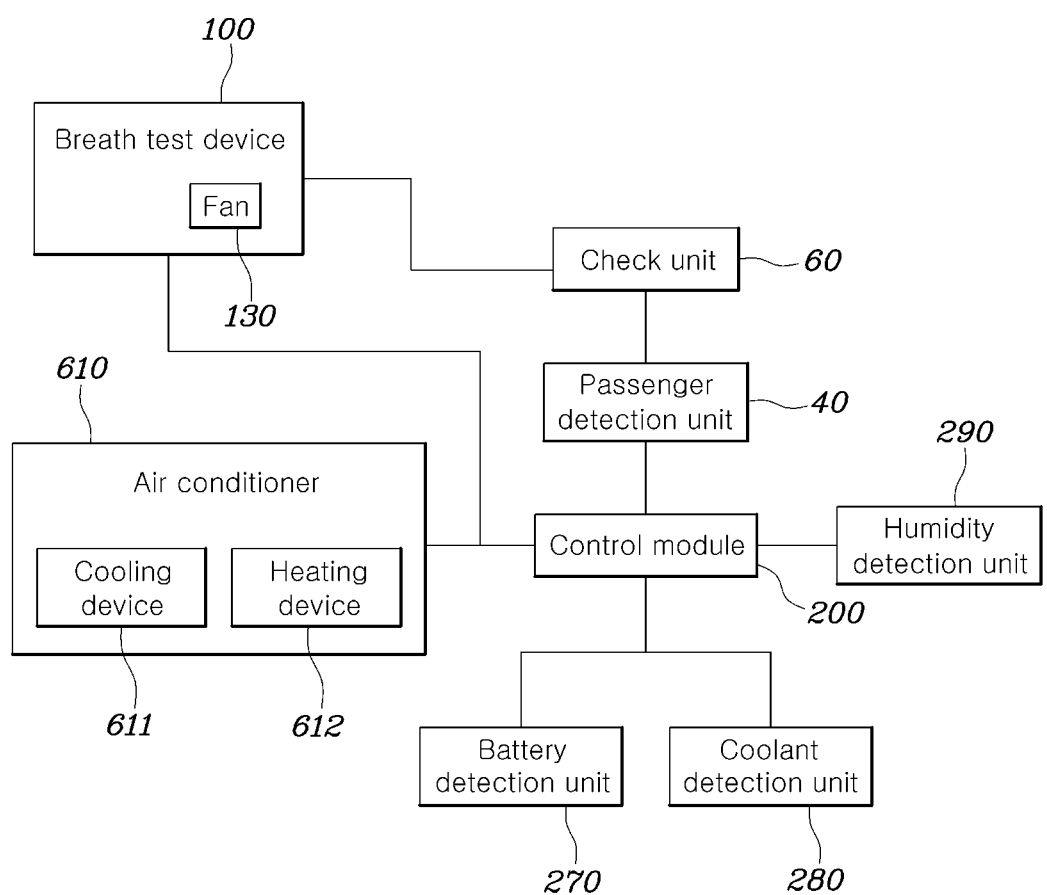
FIG. 13 is a block diagram of a breath test device sterilization system included in a drunk driving prevention system according to an embodiment of the present disclosure.

FIG. 13 is a block diagram of a breath test device 100 sterilization system included in a drunk driving prevention system according to an embodiment of the present disclosure.

A preferred embodiment of the breath test device 100 sterilization system included in the drunk driving prevention system according to the present disclosure will be described with reference to FIG. 13.

A breath test device 100 may be provided in the vehicle to prevent the driver from drinking and driving, and the driver may measure the drunk state through the breath test device 100 and drive the vehicle if the driver is not in the drunk state.

The breath test device 100 may detect the driver's blood alcohol concentration through a breath exhaled by the driver, and foreign substances such as saliva may be introduced into the breath test device 100 when the driver exhales, which may cause malfunction of the breath test device 100.

In order to prevent this, a breath test device 100 sterilization system of a vehicle according to the present disclosure may control the vehicle air conditioner 610 to sterilize the breath test device 100.

The breath test device 100 sterilization system of a vehicle according to the present disclosure may include: a check unit 60 for checking whether or not the breath test device 100, which is provided in the vehicle and has a fan 130 inside thereof to suck the driver's breath, thereby measuring the drunk state, operates; a passenger detection unit 40 for detecting whether or not a passenger is on board; and a control module 200 that, if the check unit 60 identifies that the breath test device 100 has been operated and if the passenger detection unit 40 detects that all passengers have alighted, controls the air conditioner 610 of the vehicle to discharge hot air above a predetermined temperature therefrom, thereby sanitizing the inside of the breath test device 100.

The check unit 60 may check whether or not the breath test device 100 has been operated, and the passenger detection unit 40 may detect that an occupant is in the vehicle.

The passenger detection unit 40 may be connected to a camera sensor provided inside the vehicle to detect whether or not the driver of the vehicle is on board, and may be connected to a sensor capable of detecting the driver, such as a CO2 sensor of the vehicle or a pressure sensor mounted on the seat, as well as the camera sensor, to detect whether or not the driver is on board.

If the check unit 60 identifies that the breath test device 100 has been operated and if the passenger detection unit 40 detects that all occupants have alighted, the control module 200 may control the air conditioner 610 of the vehicle to discharge hot air above a predetermined temperature therefrom.

The predetermined temperature may be 80 degrees C. or more to sterilize the breath test device 100, and may be set to a temperature of 85 degrees or less so as to prevent damages to the interior materials of the vehicle. This temperature may be set by the designer of the system depending on the conditions of the vehicle.

Through this, the hot air discharged from the air conditioner 610 may be introduced into the breath test device 100 to sterilize foreign substances such as driver's saliva remaining inside the breath test device 100 or may be sent to the outside of the breath test device 100, thereby sanitizing the breath test device 100 in the absence of occupants.

When controlling the air conditioner 610 to discharge hot air above a predetermined temperature, the control module 200 may control the breath test device 100 such that the fan 130 of the breath test device 100 is operated to introduce the air discharged from the air conditioner 610 into the breath test device 100.

When the driver blows a breath into the breath test device 100, the fan 130 provided therein is operated to suck the driver's breath into the breath test device 100, thereby accurately measuring the drunk state of the driver.

When the control module 200 operates the air conditioner 610 to sterilize the breath test device 100, the fan 130 provided in the breath test device 100 may be operated to immediately suck the hot air discharged from the air conditioner 610 into the breath test device 100.

Through this, the operation of the air conditioner 610 may be minimized, thereby saving energy.

The control module 200 may control the air conditioner 610 in an indoor air circulation mode while controlling the air conditioner 610 to discharge hot air above a predetermined temperature.

When operating the air conditioner 610 to sterilize the breath test device 100, the control module 200 may perform control such that the air circulation mode of the vehicle switches to the indoor air circulation mode, thereby preventing the air discharged from the air conditioner 610 from leaking to the outside of the vehicle.

Through this, the hot air discharged from the air conditioner 610 is prevented from leaking to the outside, so that the operation of the air conditioner 610 may be minimized, thereby saving energy.

When controlling the air conditioner 610 to discharge the hot air above a predetermined temperature, the control module 200 may control the air conditioner 610 such that the discharged air is directed to the breath test device 100.

The breath test device 100 may be usually located adjacent to the steering wheel or the driver's seat, and the control module 200 may perform control such that the blowing direction of the air conditioner 610 is changed toward the position where the breath test device 100 is located when operating the air conditioner 610 to sterilize the breath test device 100.

Through this, the operation of the air conditioner 610 may be minimized, thereby saving energy.

A humidity detection unit 290 for detecting the humidity inside the vehicle may be further included, and the control module 200 may control a cooling device or heating device 612 included in the air conditioner 610 on the basis of the humidity detected by the humidity detection unit 290, thereby controlling the air conditioner 610 to discharge hot air above a predetermined temperature.

The humidity detection unit 290 may be connected to a humidity sensor provided inside the vehicle to detect the humidity inside the vehicle.

The air conditioner 610 may cool or heat air through an eta core serving as a cooling device 611 and a heater core serving as a heating device 612 and discharge the same into the vehicle.

In order to sterilize the inside of the breath test device 100, dry and hot air must be introduced into the vehicle.

Dry air may be discharged when the cooling device 611 is operated, and the control module 200 may operate only the heating device 612 according to the humidity inside the vehicle detected by the humidity detection unit 290 to discharge hot air or operate both the cooling device 611 and the heating device 612 to discharge hot and dry air, thereby sterilizing the breath test device 100.

If the humidity detection unit 290 detects the humidity is higher than a predetermined humidity, the control module 200 may control the air conditioning device 610 such that the cooling device and the heating device 612 included in the air conditioning device 610 are operated to discharge dry air.

If the humidity detection unit 290 detects that the humidity inside the vehicle is higher than the predetermined humidity so that the inside of the vehicle is in a humid state, the control module 200 may operate both the cooling device 611 and the heating device 612 to discharge hot and dry air into the vehicle through the air conditioner 610.

Through this, the inside of the breath test device 100 may be sterilized by hot and dry air, maintaining the breath test device 100 clean.

If the humidity detection unit 290 detects that the humidity is lower than the predetermined humidity, the control module 200 may control the air conditioner 610 such that only the heating device 612 included in the air conditioner 610 is operated to discharge hot air.

If the humidity detection unit 290 detects that the humidity inside the vehicle is less than the predetermined humidity so that the inside of the vehicle is in a dry state, the air conditioner 610 may operate only the heating device 612 to discharge only hot air, thereby sterilizing the breath test device 100.

Through this, there is an effect of preventing unnecessary energy consumption by operating only the heating device 612 without operating the cooling device 611.

The following embodiment may be applied to an internal combustion engine vehicle.

A coolant detection unit 280 for detecting the temperature of an engine coolant may be further included, and the control module 200 may stop the operation of the air conditioner 610 if the temperature of the coolant detected by the coolant detection unit 280 is less than or equal to a predetermined temperature.

In the case of an internal combustion engine vehicle, the heating device 612 of the air conditioner 610 may be operated through the engine coolant of the vehicle. The engine coolant may absorb heat from the engine and heat the air sucked in from the outside using the absorbed heat, and the heated air may be introduced into the vehicle through a filter.

At this time, if the temperature of the coolant is lower than a predetermined temperature due to a short driving distance of the vehicle, the coolant detection unit 280 may detect the temperature of the coolant, and if the detected temperature is lower than a predetermined temperature, the control module 200 may perform control such that the air conditioner 610 is not operated, thereby preventing unnecessary fuel wastage without operating the engine of the vehicle.

The following embodiment may be applied to an electric vehicle or a hybrid vehicle in which the cooling device 611 or the heating apparatus 612 of the air conditioner 610 is operated using power of a battery provided in the vehicle.

A battery detection unit 270 for detecting the remaining amount of the battery mounted to the vehicle may be further included, and the control module 200 may stop the operation of the air conditioner 610 if the remaining amount of the battery detected by the battery detecting unit 270 is less than or equal to a predetermined value.

The heating device 612 of the air conditioner 610 consumes a large amount of power of the battery, and when the battery of the vehicle loses its power, the vehicle may not operate normally after the driver gets on the electric vehicle or hybrid vehicle.

To prevent this, the battery detection unit 270 may measure the remaining amount of the battery mounted to the vehicle and control the air conditioner 610 not to operate if the remaining amount of the battery less than a predetermined value or stop the operation of the air conditioner 610 if the remaining amount of the battery is lowered below a predetermined value during operation.

Figure 14:
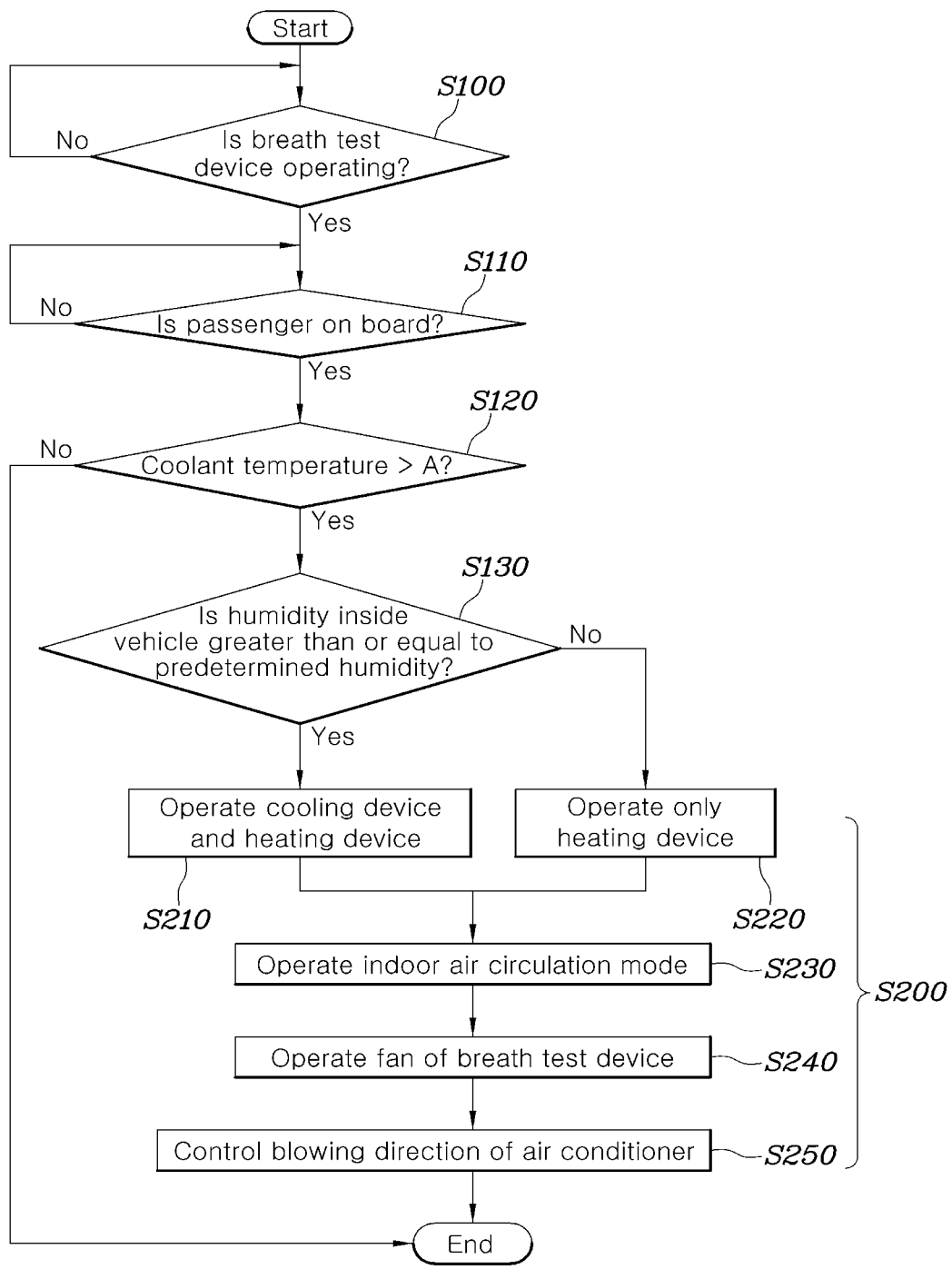
FIGS. 14 to 15 are flowcharts illustrating a method of sterilizing a breath test device of a drunk driving prevention system according to various embodiments of the present disclosure.
Figure 15:
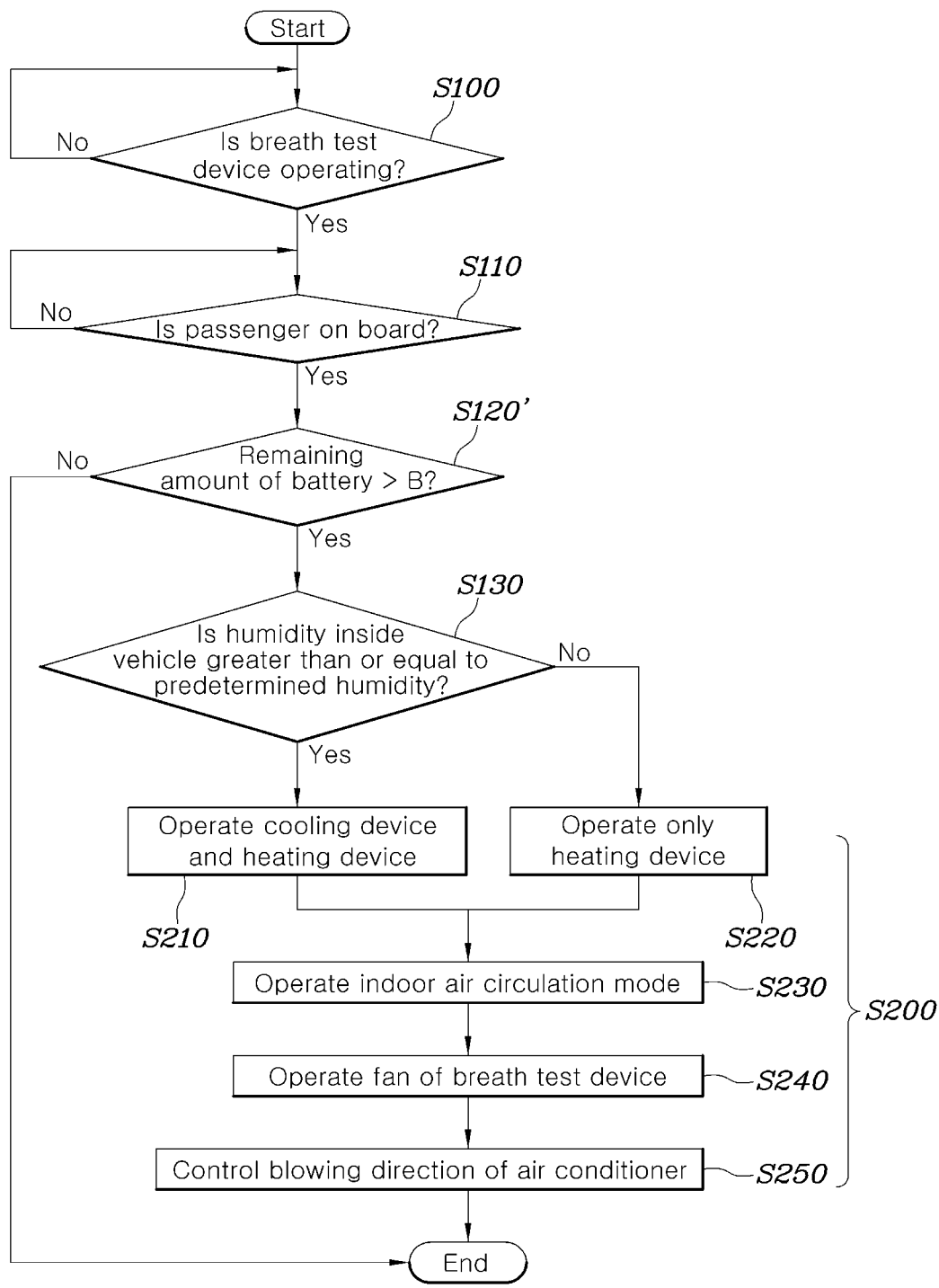

FIGS. 14 to 15 are flowcharts illustrating a method of sterilizing a breath test device 100 of a drunk driving prevention system according to various embodiments of the present disclosure.

A preferred embodiment of a method of sterilizing a breath test device 100 of a vehicle according to the present disclosure will be described with reference to FIGS. 14 to 15.

A method of sterilizing the breath test device 100 of the drunk driving prevention system according to the present disclosure may include: a step S100 of checking whether or not the breath test device 100 provided in the vehicle has been operated; a step S110 of detecting whether or not a passenger is on board; and a step S200 of, if it is identified that the breath test device 100 has been operated in the check step S100 and if it is detected that all passengers have alighted in the detection step S110, controlling the air conditioner 610 of the vehicle to discharge hot air above a predetermined temperature to sterilize the inside of the breath test device 100.

The control step S200 may include a step S240 of controlling the breath test device 100 such that the fan 130 of the breath test device 100 is operated when controlling the air conditioner 610 to discharge the hot air above a predetermined temperature so that the air discharged from the air conditioner 610 is introduced into the breath test device 100.

The control step S200 may include a step S230 of controlling the air conditioner 610 in an indoor air circulation mode while controlling the air conditioner 610 to discharge the hot air above a predetermined temperature.

The control step S200 may include a step S250 of controlling the air conditioner 610 such that the discharged air is directed to the breath test device 100 when controlling the air conditioner 610 to discharge the hot air above a predetermined temperature.

A step S130 of detecting the humidity inside the vehicle may be further included, and in the control step S200, the air conditioner 610 may be controlled such that the cooling device 611 or the heating device 612 included in the air conditioner 610 is controlled on the basis of the humidity detected by the humidity detection unit 290 to discharge hot air above a predetermined temperature therefrom.

The control step S200 may include a step S210 of, if the humidity is detected to be greater than or equal to a predetermined humidity in the step S130 of detecting the humidity, controlling the air conditioner 610 such that the cooling device 611 and the heating device 612 included in the air conditioner 610 are operated to discharge dry air.

The control step S200 may include a step S220 of, if the humidity is detected to be less than a predetermined humidity in the step S130 of detecting the humidity, controlling the air conditioner 610 such that only the heating device 612 included in the air conditioner 610 is operated to discharge hot air.

A step S120 of detecting the temperature of an engine coolant may be further included, and in the control step S200, if the temperature of the coolant detected in the step S120 of detecting the temperature of the engine coolant is less than or equal to a predetermined temperature, the air conditioner 610 may be stopped.

A step S120' of detecting the remaining amount of a battery mounted to the vehicle may be further included, and in the control step S200, if the remaining amount of the battery detected in the step S120' of detecting the remaining amount of the battery is less than or equal to a predetermined value, the air conditioner 610 may be stopped.

Although the present disclosure has been described and illustrated in conjunction with particular embodiments thereof, it will be apparent to those skilled in the art that various improvements and modifications may be made to the present disclosure without departing from the technical idea of the present disclosure defined by the appended claims.

What is claimed is:

1. A system for preventing drunk driving of a vehicle, comprising:
    a breath test device configured to detect carbon dioxide and alcohol content in a driver's breath when the driver performs breath authentication;
    an alcohol detection unit configured to detect the driver's inebriation through the breath test device;
    a computation unit configured, when the alcohol detection unit detects that the driver is in a drunk state, to compute a driving-possible time at which the driver's drunk state is resolved in the future so that driving is possible for the driver; and
    a notification unit configured to output the driving-possible time or whether driving is possible for the driver through an infotainment system of the vehicle or the driver's terminal,
    wherein the notification unit is configured to set the driving-possible time based on location information of the driver detected through a function of a GPS provided in the driver's terminal.

2. The system of claim 1, further comprising an input unit configured to receive, from the driver, a signal notification intention,
    wherein, when the signal notification intention is received by the input unit, the notification unit provides the driving-possible time or whether driving is possible for the driver at the driving-possible time through the infotainment system of the vehicle or the driver's terminal.

3. The system of claim 1, further comprising a passenger detection unit configured to detect whether the driver is on board through a camera sensor or a seat sensor provided in the vehicle,
    wherein, when the passenger detection unit detects that the driver is on board, the notification unit provides the driving-possible time or whether driving is possible for the driver at the driving-possible time through the infotainment system of the vehicle.

4. The system of claim 1, wherein the notification unit is configured to:
    determine the driver's sleep state based on whether the driver's terminal is operational or nonoperational; and
    provide whether driving is possible for the driver after the driver's wake-up time detected based on whether the terminal is operational or nonoperational.

5. The system of claim 1, further comprising a control module configured to determine the driver's inebriation from an alcohol concentration detected by the breath test device to determine whether the breath authentication is complete, and, when the breath authentication fails, restrict starting of the vehicle,
    wherein the control module comprises an air quality judgment control unit configured to check an indoor air quality based on an amount of the carbon dioxide detected by the breath test device and perform a predetermined air quality control depending on the detected amount of carbon dioxide.

6. The system of claim 5, wherein the air quality judgment control unit is configured to:
    set three reference values with respect to the detected amount of the carbon dioxide, the three references values including first, second and third reference values;
    output a notification message when the detected amount of the carbon dioxide reaches the first reference value;
    output an alarm when the detected amount of the carbon dioxide reaches the second reference value; and
    control the vehicle to switch to an outdoor air circulation mode when the detected amount of the carbon dioxide reaches the third reference value.

7. The system of claim 5, wherein the air quality judgment control unit is configured to:
    check the amount of the carbon dioxide detected after the vehicle is stopped; and
    when the amount of the carbon dioxide detected after the vehicle is stopped meets or exceeds a predetermined reference value, provide a notification of a neglected occupant to the driver.

8. The system of claim 1, further comprising:
    a check unit configured to check whether the breath test device operates, the breath test device disposed at the vehicle and including a fan configured to suck the driver's breath;
    a passenger detection unit configured to detect whether a passenger is on board; and
    a control module configured to control an air conditioner of the vehicle to discharge hot air having a temperature above a predetermined temperature to sterilize an inside of the breath test device when the check unit identifies that the breath test device has been operated and the passenger detection unit detects that all passengers have alighted.

9. The system of claim 8, further comprising a humidity sensor configured to detect a humidity inside the vehicle,
    wherein the control module is configured to control the air conditioner to discharge the hot air by controlling a cooling device or heating device included in the air conditioner based on the humidity detected by the humidity sensor.

10. A method of preventing drunk driving of a vehicle, comprising:
    detecting a driver's inebriation through a breath test device provided in a vehicle;
    when the driver is detected to be in a drunk state, computing a driving-possible time at which the driver's drunk state is resolved in the future so that driving is possible for the driver;

after computing the driving-possible time, detecting location of the driver through the driver's terminal;
setting the driving-possible time based on the detected location of the driver; and
outputting the driving-possible time or whether driving is possible for the driver through an infotainment system of the vehicle or the driver's terminal.

11. The drunk driving prevention method of claim 10, further comprising:
receiving, from the driver, a signal notification intention; and
in response to receiving the signal notification intention, providing the driving-possible time or whether driving is possible at the driving-possible time through the infotainment system of the vehicle or the driver's terminal.

12. The drunk driving prevention method of claim 10, wherein:
detecting the drunk state comprises measuring the driver's blood alcohol concentration detected by the breath test device,
computing the driving-possible time including detecting, using an alcohol detection unit, the driver's blood alcohol concentration, and
the driving-possible time is computed based on driver's physical information collected previously and the detected driver's blood alcohol concentration.

13. The drunk driving prevention method of claim 10, further comprising detecting whether the driver is on board through a camera sensor or a seat sensor provided in the vehicle,
wherein outputting the driving-possible time or whether driving is possible for the driver comprises providing the driving-possible time or whether driving is possible at the driving-possible time through the infotainment system of the vehicle when it is detected that the driver is on board.

14. The drunk driving prevention method of claim 13, wherein outputting the driving-possible time or whether driving is possible for the driver comprises whether driving is possible through the driver's terminal at the driving-possible time when it is detected that the driver has alighted.

15. The drunk driving prevention method of claim 10, wherein:
detecting the location comprises determining whether the detected location of the driver is a predetermined location, and
outputting the driving-possible time or whether driving is possible for the driver comprises providing whether driving is possible for the driver after a predetermined driver's wake-up time when the location of the driver is the predetermined location.

16. The drunk driving prevention method of claim 10, further comprising, after computing the driving-possible time or whether driving is possible for the driver, determining the driver's sleep state based on whether the driver's terminal is operational or nonoperational,
wherein outputting the driving-possible time or whether driving is possible for the driver comprises, when it is determined that the driver is asleep, providing whether driving is possible after the driver's wake-up time detected based on whether the driver's terminal is operational or nonoperational.

17. The drunk driving prevention method of claim 10, further comprising, after outputting the driving-possible time or whether driving is possible for the driver, determining the driver's sleep state by detecting illuminance of light through an illuminance sensor provided in the terminal,
wherein outputting the driving-possible time or whether driving is possible for the driver comprises determining that the driver is asleep when the detected illuminance of light is low and providing whether driving is possible for the driver after the driver's wake-up time determined from determining the driver's sleep state.

18. The drunk driving prevention method of claim 10, further comprising determining the driver's sleep state through a heart rate sensor provided in the driver's terminal to measure the driver's heart rate,
wherein outputting the driving-possible time or whether driving is possible for the driver comprises providing whether driving is possible for the driver after the driver's wake-up time detected based on the determined driver's sleep state.

* * * * *